United States Patent [19]

Schallner et al.

[11] Patent Number: 5,024,694
[45] Date of Patent: Jun. 18, 1991

[54] HERBICIDAL N-ARYL NITROGEN HETEROCYCLES HAVING FLUORINE-CONTAINING SUBSTITUENTS

[75] Inventors: Otto Schallner, Monheim; Michael Negele, Cologne; Hans-Joachim Santel, Leverkusen; Klaus Lürssen, Bergisch-Gladbach; Robert R. Schmidt, Bergisch-Gladbach; Birgit Krauskopf, Bergisch-Gladbach, all of Fed. Rep. of Germany

[73] Assignee: Bayer Aktiengesellschaft, Leverkusen, Fed. Rep. of Germany

[21] Appl. No.: 476,224

[22] Filed: Feb. 6, 1990

[30] Foreign Application Priority Data

Feb. 18, 1989 [DE] Fed. Rep. of Germany ....... 3905006

[51] Int. Cl.$^5$ .................. C07D 209/48; C07D 209/46; C07D 207/452; C07D 487/04
[52] U.S. Cl. .......................................... 71/95; 71/92; 548/465; 548/476; 548/472; 548/512; 548/513; 548/543; 548/549; 546/121
[58] Field of Search .................. 546/121; 548/465; 71/92, 95

[56] References Cited

U.S. PATENT DOCUMENTS 4,536,209 8/1985 Jikihara .................................. 71/92
4,670,046 6/1987 Magano .................................. 71/96

Primary Examiner—Mark L. Berch
Attorney, Agent, or Firm—Sprung Horn Kramer & Woods

[57] ABSTRACT

Herbicidal and plant growth-regulating N-aryl heterocycles of the formula

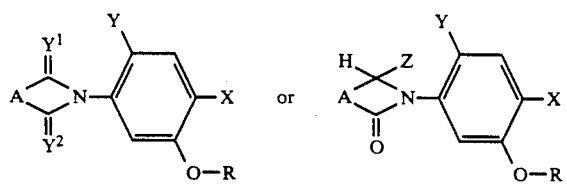

where
A represents one of the groupings

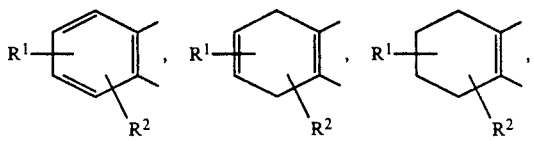

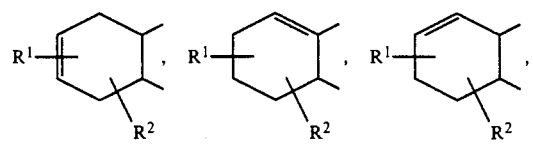

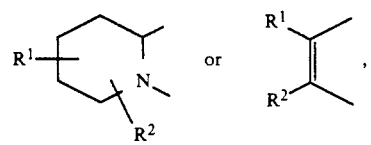

where
$R^1$ and $R^2$ in each case independently of one another represent hydrogen, halogen, halogenoalkyl or alkyl,
$Y^1$ and $Y^2$ in each case represent oxygen or sulphur and
Z represents hydrogen, hydroxyl or chlorine, R represents in each case optionally branched alkyl, alkenyl, cycloalkyl, cycloalkenyl, cycloalkylalkyl or cycloalkenylalkyl in each case interrupted by at least one oxygen atom and in each case substituted by at least one fluorine atom,
X represents hydrogen or halogen and
Y represents hydrogen or halogen.

11 Claims, No Drawings

HERBICIDAL N-ARYL NITROGEN HETEROCYCLES HAVING FLUORINE-CONTAINING SUBSTITUENTS

The present invention relates to new N-aryl nitrogen heterocycles having fluorine-containing substituents, processes for their preparation and their use as herbicides and as plant growth regulators and also to new intermediates.

It is known that certain nitrogen heterocycles, such as, for example, 5-tert-butyl-3-(2,4-dichloro-5-isopropoxy-phenyl)-1,3,4-oxadiazol-2-one (oxadiazone/-®Ronstar) exhibit herbicidal properties (compare U.S. Pat. No. 3,835,862).

However, the action of this compound is unsatisfactory at low application rates or active compound concentrations.

The new N-aryl nitrogen heterocycles having fluorine-containing substituents of the general formula (I)

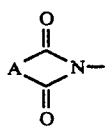

(I)

in which
Het represents one of the heterocyclic groupings

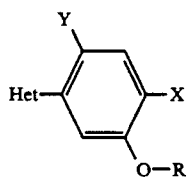

where
A represents one of the groupings

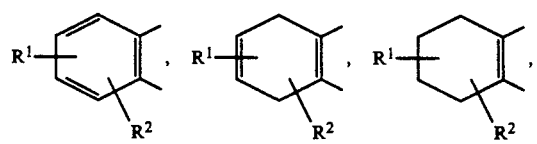

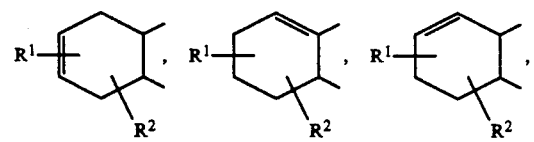

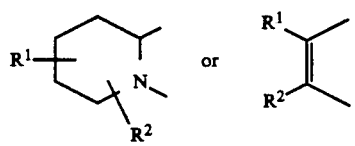

where
$R^1$ and $R^2$ in each case independently of one another represent hydrogen, halogen, halogenoalkyl or alkyl,
$Y^1$ and $Y^2$ in each case represent oxygen or sulphur and
Z represents hydrogen, hydroxyl or chlorine, R represents in each case optionally branched alkyl, alkenyl, cycloalkyl, cycloalkenyl, cycloalkylalkyl or cycloalkenylalkyl in each case interrupted by at least one oxygen atom and in each case substituted by at least one fluorine atom,
X represents hydrogen or halogen and
Y represents hydrogen or halogen, have now been found.

It has further been found that the new N-aryl nitrogen heterocycles having fluorine-containing substituents of the general formula (I) are obtained when
(a) in the case in which Het represents the grouping

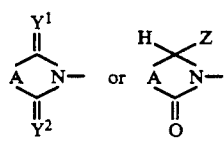

and
A, R, X and Y have the abovementioned meanings, cyclic anhydrides of the general formula (II)

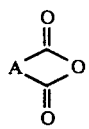

(II)

in which
A has the abovementioned meaning, are reacted with arylamines of the general formula (III)

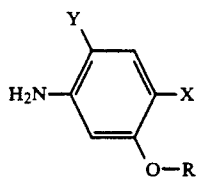

(III)

in which
R, X and Y have the abovementioned meanings, if appropriate in the presence of a diluent and if appropriate in the presence of a reaction auxiliary, or when
(b) in the case in which Het represents the grouping

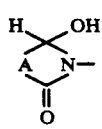

and
A, R, X and Y have the abovementioned meanings, substituted arylimides of the general formula (Ia)

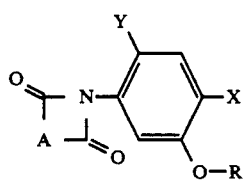

(Ia)

in which

A, R, X and Y have the abovementioned meanings, are reacted with a reducing agent, if appropriate in the presence of a diluent, or when (c) in the case in which Het represents the grouping

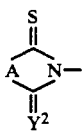

and

A, R, X, Y and $Y^2$ have the abovementioned meanings, substituted arylimides of the general formula (Ia)

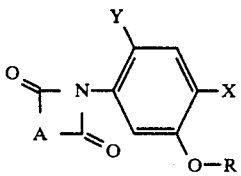  (Ia)

in which

A, R, X and Y have the abovementioned meanings, are reacted with a sulphurizing agent, if appropriate in the presence of a diluent, or when (d) in the case in which Het represents the grouping

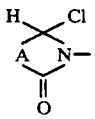

and

A, R, X and Y have the abovementioned meanings, N-aryl nitrogen heterocycles of the general formula (Ib)

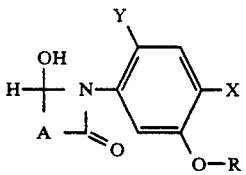  (Ib)

in which

A, R, X and Y have the abovementioned meanings, are reacted with thionyl chloride, if appropriate in the presence of a diluent and if appropriate in the presence of a reaction auxiliary, or when (e) in the case in which Het represents the grouping

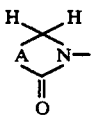

and

A, R, X and Y have the abovementioned meanings, N-aryl nitrogen heterocycles of the general formula (Ic)

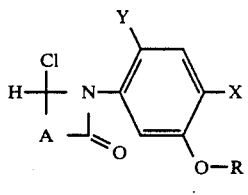  (Ic)

in which

A, R, X and Y have the abovementioned meanings, are reacted with hydrogen, in the presence of a catalyst and also if appropriate in the presence of a diluent and if appropriate in the presence of an acid-binding agent, or when (f) in the case in which Het represents the grouping

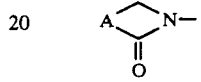

and

A, R, X and Y have the abovementioned meanings, hydroxyarylimides of the general formula (IV)

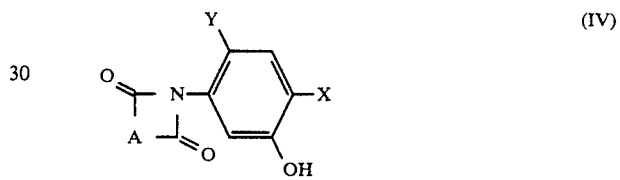  (IV)

in which

A, X and Y have the abovementioned meanings, are reacted with alkylating agents of the general formula (V)

$X^1$-R    (V)

in which

R has the abovementioned meaning and $X^1$ represents a nucleophilic leaving group, if appropriate in the presence of an acid acceptor and if appropriate in the presence of a diluent, or when (g) in the case in which Het represents the grouping

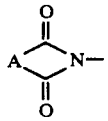

and

A, R and Y have the abovementioned meanings and X represents halogen, substituted arylimides of the general formula (Id)

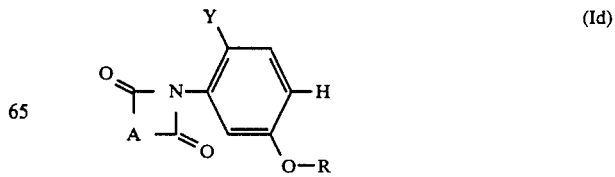  (Id)

in which
A, R and Y have the abovementioned meanings, are reacted with a halogenating agent, if appropriate in the presence of a catalyst and if appropriate in the presence of a diluent, or when
(h) in the case in which Het represents the grouping

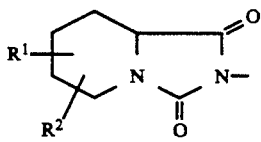

and
R, $R^1$, $R^2$, X and Y have the abovementioned meanings, arylamines of the general formula (III)

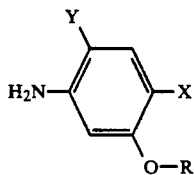

(III)

in which
R, X and Y have the abovementioned meanings, are reacted with chloroformates of the general formula (VI)

$R^3O\text{-}CO\text{-}Cl$         (VI)

in which
$R^3$ represents $C_1$-$C_4$-alkyl, benzyl or phenyl, if appropriate in the presence of an acid acceptor and if appropriate in the presence of a diluent and the arylurethanes formed in this case of the general formula (VII)

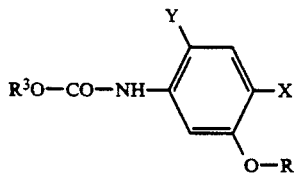

(VII)

in which
R, $R^3$, X and Y have the abovementioned meanings, are reacted with piperidine-2-carboxylates of the general formula (VIII)

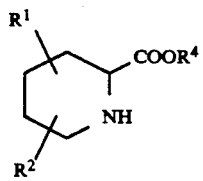

(VIII)

in which
$R^1$ and $R^2$ have the abovementioned meanings and
$R^4$ represents $C_1$-$c_4$-alkyl, if appropriate in the presence of a diluent.

Finally, it has been found that the new N-aryl nitrogen heterocycles having fluorine-containing substituents of the general formula (I) exhibit herbicidal and plant growth-regulating properties.

Surprisingly, the N-aryl nitrogen heterocycles having fluorine-containing substituents of the formula (I) according to the invention are substantially more strongly active against weeds than 5-tert-butyl-3-(2,4-dichloro-5-isopropoxy-phenyl)-1,3,4-oxadiazol-2-one, which is a structurally similar previously known active compound with the same type of action.

The invention preferably relates to compounds of the formula (I), in which Het represents one of the heterocyclic groupings

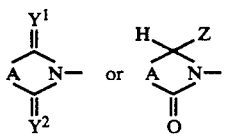

where
A represents one of the groupings

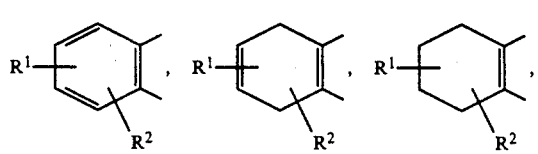

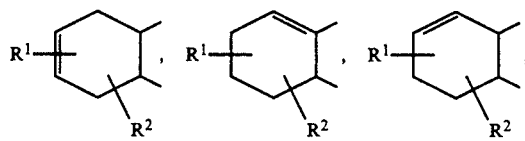

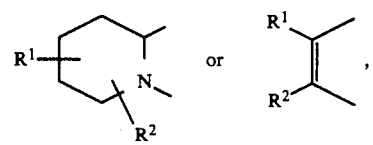

where
$R^1$ and $R^2$ in each case independently of one another represent hydrogen, fluorine, chlorine, bromine or in each case straight-chain or branched alkyl or halogenoalkyl each having 1 to 3 carbon atoms and in the case of halogenoalkyl having 1 to 5 identical or different halogen atoms, in particular fluorine or chlorine, $Y^1$ and $Y^2$ represent oxygen or sulphur, Z represents hydrogen, hydroxyl or chlorine, R represents in each case optionally branched alkyl, alkenyl, cycloalkyl, cycloalkenyl, cycloalkylalkyl or cycloalkenylalkyl each having up to 20, preferably up to 15, and in particular up to 10, carbon atoms and in each case interrupted by 1 to 4 oxygen atoms and in each case substituted by 1 to 5 fluorine atoms, X represents hydrogen, fluorine, chlorine or bromine, and Y represents hydrogen, fluorine or chlorine.

The invention relates in particular to compounds of the formula (I), in which Het represents one of the heterocyclic groupings

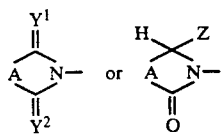

where

A represents one of the groupings

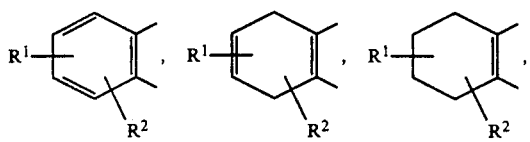

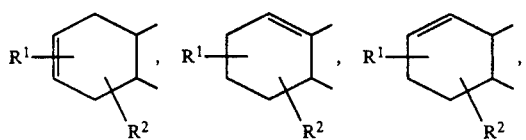

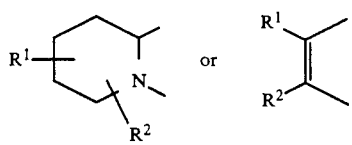

where

R¹ and R² in each case independently of one another represent hydrogen, methyl or trifluoromethyl,
Y¹ and Y² represent oxygen or sulphur,
Z represents hydrogen, hydroxyl or chlorine,
R represents in each case optionally branched oxaalkyl or dioxaalkyl each having up to 10, in particular up to 5, 6, 7 or 8 carbon atoms, and in each case substituted by 2 to 4 fluorine atoms,
X represents hydrogen, chlorine or bromine and
Y represents hydrogen or fluorine.

In the definition ranges enumerated, the following heterocycles are very particularly preferred:

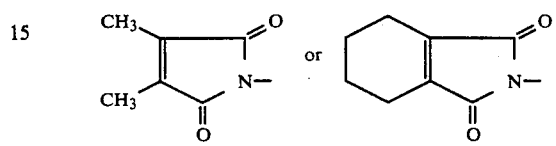

Examples of the compounds of the formula (I) according to the invention are listed in Table 1 below-also compare the preparation examples.

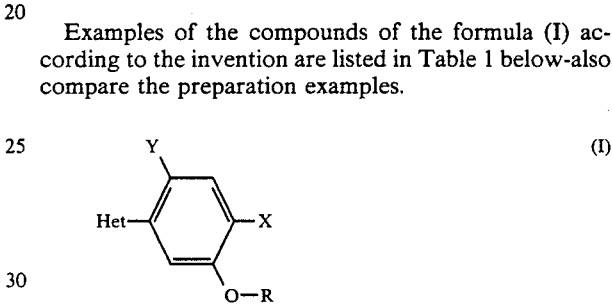

TABLE 1

| Examples of the compounds of the formula (I) | | | | |
|---|---|---|---|---|
| Het | | X | Y | R |
| cyclohexene-dicarboximide | | H | H | —CH₂CH₂—O—CH₂CH₂—O—CHF₂ |
| cyclohexene-dicarboximide | | H | H | —CH₂CH₂—O—CH₂CH₂—O—CH₂CF₃ |
| cyclohexene-dicarboximide | | F | F | —CH₂CH₂—O—CH₂CH₂—O—CHF₂ |
| cyclohexene-dicarboximide | | F | F | —CH₂CH₂—O—CH₂CH₂—O—CH₂CF₃ |
| cyclohexene-dicarboximide | | Cl | H | —CH₂CH₂—O—CH₂CH₂—O—CHF₂ |

TABLE 1-continued
Examples of the compounds of the formula (I)

| Het | X | Y | R |
|---|---|---|---|
| 4,5,6,7-tetrahydroisoindole-1,3-dione | Cl | F | —CH₂CH₂—O—CH₂CH₂—O—CH₂CF₃ |
| 4,5,6,7-tetrahydroisoindole-1,3-dione | Br | H | —CH₂CH₂—O—CH₂CH₂—O—CHF₂ |
| 4,5,6,7-tetrahydroisoindole-1,3-dione | Br | F | —CH₂CH₂—O—CH₂CH₂—O—CH₂CF₃ |
| 4,5,6,7-tetrahydroisoindole-1,3-dione | Cl | H | —CH₂CH₂—O—CH₂CF₃ |
| 4,5,6,7-tetrahydroisoindole-1,3-dione | Cl | F | —CH₂CH₂—O—CH₂CF₃ |
| 4,5,6,7-tetrahydroisoindole-1,3-dione | Cl | F | —CH₂CH₂—O—CH₂—CH(CH₂F)₂ |
| 4,5,6,7-tetrahydroisoindole-1,3-dione | Cl | F | —CH(CH₃)CH₂—O—CH₂CF₃ |
| 4,5,6,7-tetrahydroisoindole-1,3-dione | Cl | F | —CH(C₂H₅)CH₂—O—CH₂CF₃ |
| 4,5,6,7-tetrahydroisoindole-1,3-dione | Cl | F | —CH(CH₂F)CH₂—O—CH₂CF₃ |
| 7-methyl-4,5,6,7-tetrahydroisoindole-1,3-dione | Cl | F | —CH₂CH₂—O—CH₂CH₂—O—CHF₂ |

Note: chemical structures rendered as text descriptions; R groups contain subscripts rendered with Unicode for readability — see LaTeX forms: $-\mathrm{CH_2CH_2-O-CH_2CH_2-O-CH_2CF_3}$, $-\mathrm{CH_2CH_2-O-CH_2CH_2-O-CHF_2}$, $-\mathrm{CH_2CH_2-O-CH_2CF_3}$, $-\mathrm{CH_2CH_2-O-CH_2-CH(CH_2F)_2}$, $-\mathrm{CH(CH_3)CH_2-O-CH_2CF_3}$, $-\mathrm{CH(C_2H_5)CH_2-O-CH_2CF_3}$, $-\mathrm{CH(CH_2F)CH_2-O-CH_2CF_3}$.

TABLE 1-continued

Examples of the compounds of the formula (I)

| Het | X | Y | R |
|---|---|---|---|
| 7-methyl-hexahydroisoindole-1,3-dione | F | F | —CH$_2$CH$_2$—O—CH$_2$CH$_2$—O—CH$_2$CF$_3$ |
| 7-methyl-hexahydroisoindole-1,3-dione | Br | F | —CH$_2$CH$_2$—O—CH$_2$CH$_2$—O—CHF$_2$ |
| 7-methyl-hexahydroisoindole-1,3-dione | Cl | F | —CH$_2$CH$_2$—O—CH$_2$CF$_3$ |
| 7-methyl-hexahydroisoindole-1,3-dione | Cl | F | —CH$_2$CH$_2$—O—CHCF$_2$ |
| 5-methyl-hexahydroisoindole-1,3-dione | F | F | —CH$_2$CH$_2$—O—CH$_2$CH$_2$—O—CHF$_2$ |
| 5-methyl-hexahydroisoindole-1,3-dione | H | H | —CH$_2$CH$_2$—O—CH$_2$CH$_2$—O—CH$_2$CF$_3$ |
| 5-methyl-hexahydroisoindole-1,3-dione | Cl | F | —CHCH$_2$—O—CH$_2$CF$_3$<br>　　\|<br>　　CH$_3$ |
| 5-methyl-hexahydroisoindole-1,3-dione | F | F | —CHCH$_2$—O—CH$_2$CF$_3$<br>　　\|<br>　　CH$_2$F |
| 5-methyl-hexahydroisoindole-1,3-dione | Cl | F | —CH$_2$CH$_2$—O—CH$_2$CH$_2$—O—CH$_2$CF$_3$ |
| 5-methyl-hexahydroisoindole-1,3-dione | Cl | F | —CH$_2$CH$_2$—O—CH$_2$CF$_3$ |

TABLE 1-continued

| Examples of the compounds of the formula (I) | | | |
|---|---|---|---|
| Het | X | Y | R |
| 5-methyl-3a,4,7,7a-tetrahydroisoindole-1,3-dione (4-methyl-hexahydrophthalimide) | Cl | F | —CH$_2$CH$_2$—O—CHF$_2$ |
| 3a,4,7,7a-tetrahydroisoindole-1,3-dione | F | F | —CH$_2$CH$_2$—O—CH$_2$CH$_2$—O—CH$_2$CF$_3$ |
| 3a,4,7,7a-tetrahydroisoindole-1,3-dione | H | H | —CH$_2$CH$_2$—O—CH$_2$CH$_2$—O—CH$_2$CF$_3$ |
| 3a,4,7,7a-tetrahydroisoindole-1,3-dione | Br | F | —CH$_2$CH$_2$—O—CH$_2$CH$_2$—O—CH$_2$CF$_3$ |
| 3a,4,7,7a-tetrahydroisoindole-1,3-dione | Cl | F | —CH$_2$CH$_2$—O—CH$_2$CH$_2$—O—CHF$_2$ |
| 3a,4,7,7a-tetrahydroisoindole-1,3-dione | Cl | F | —CH(CH$_3$)CH$_2$—O—CH$_2$CF$_3$ |
| 3a,4,7,7a-tetrahydroisoindole-1,3-dione | Cl | F | —CH$_2$CH$_2$—O—CH$_2$CF$_3$ |
| 3a,4,7,7a-tetrahydroisoindole-1,3-dione | Cl | F | —CH(CH$_3$)CH$_2$—O—CHF$_2$ |
| 3a,4,5,7a-tetrahydroisoindole-1,3-dione | F | F | —CH$_2$CH$_2$—O—CH$_2$CH$_2$—O—CHF$_2$ |
| 3a,4,5,7a-tetrahydroisoindole-1,3-dione | H | H | —CH$_2$CH$_2$—O—CH$_2$CH$_2$—O—CH$_2$CF$_3$ |

TABLE 1-continued

Examples of the compounds of the formula (I)

| Het | X | Y | R |
|---|---|---|---|
| (cyclohexene-fused succinimide) | Cl | F | —CH(CH₂F)CH₂—O—CH₂CF₃ |
| (cyclohexene-fused succinimide) | Cl | F | —CH₂CH₂—O—CH₂CH₂—O—CH₂CF₃ |
| (cyclohexene-fused succinimide) | Cl | F | —CH(C₂H₅)CH₂—O—CH₂CF₃ |
| (cyclohexene-fused succinimide) | Cl | F | —CH₂CH₂—O—CH₂CF₃ |
| (cyclohexene-fused succinimide) | Cl | F | —CH₂CH₂—O—CHF₂ |
| (3,3-dimethyl cyclohexane-fused succinimide) | F | F | —CH₂CH₂—O—CH₂CH₂—O—CHF₂ |
| (3,3-dimethyl cyclohexane-fused succinimide) | H | H | —CH₂CH₂—O—CH₂CH₂—O—CH₂CF₃ |
| (3,3-dimethyl cyclohexane-fused succinimide) | Cl | F | —CH(CH₃)CH₂—O—CH₂CH₂—O—CHF₂ |
| (3,3-dimethyl cyclohexane-fused succinimide) | Cl | F | —CH₂CH₂—O—CH₂CH₂—O—CH₂CF₃ |
| (3,3-dimethyl cyclohexane-fused succinimide) | Br | F | —CH₂CH₂—O—CH₂CH₂—O—CHF₂ |

Note: R column formulas shown with LaTeX subscripts:
- $-\text{CH(CH}_2\text{F)CH}_2-\text{O}-\text{CH}_2\text{CF}_3$
- $-\text{CH}_2\text{CH}_2-\text{O}-\text{CH}_2\text{CH}_2-\text{O}-\text{CH}_2\text{CF}_3$
- $-\text{CH(C}_2\text{H}_5\text{)CH}_2-\text{O}-\text{CH}_2\text{CF}_3$
- $-\text{CH}_2\text{CH}_2-\text{O}-\text{CH}_2\text{CF}_3$
- $-\text{CH}_2\text{CH}_2-\text{O}-\text{CHF}_2$
- $-\text{CH}_2\text{CH}_2-\text{O}-\text{CH}_2\text{CH}_2-\text{O}-\text{CHF}_2$
- $-\text{CH(CH}_3\text{)CH}_2-\text{O}-\text{CH}_2\text{CH}_2-\text{O}-\text{CHF}_2$ TABLE 1-continued Examples of the compounds of the formula (I)

| Het | X | Y | R |
|---|---|---|---|
| 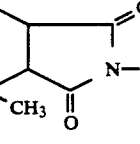 | Cl | F | —CH$_2$CH$_2$—O—CH$_2$CF$_3$ |
| 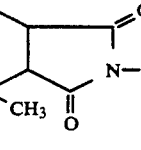 | Cl | F | —CHCH$_2$—O—CH$_2$CF$_3$<br>\|<br>CH$_2$F |
| 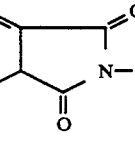 | F | F | —CH$_2$CH$_2$—O—CH$_2$CH$_2$—O—CHF$_3$ |
| 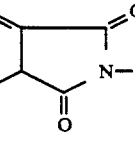 | H | H | —CH$_2$CH$_2$—O—CH$_2$CH$_2$—O—CH$_2$CF$_3$ |
| 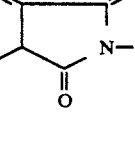 | Cl | F | —CHCH$_2$—O—CH$_2$CF$_3$<br>\|<br>CH$_3$ |
| 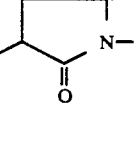 | Br | F | —CHCH$_2$—O—CH$_2$CF$_3$<br>\|<br>CH$_2$F |
| 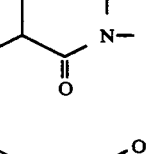 | Cl | F | —CHCH$_2$—O—CH$_2$CF$_3$<br>\|<br>C$_2$H$_5$ |
| 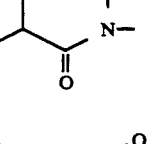 | Cl | F | —CH$_2$—CH$_2$—O—CH$_2$CF$_3$ |
| 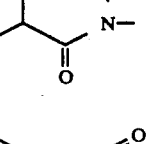 | Cl | F | —CHCH$_2$—O—CHF$_2$<br>\|<br>CH$_3$ |
| 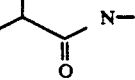 | F | F | —CH$_2$CH$_2$—O—CH$_2$CH$_2$—O—CHF$_2$ |

TABLE 1-continued

Examples of the compounds of the formula (I)

| Het | X | Y | R |
|---|---|---|---|
| [tetrahydrophthalimide] | H | H | —CH$_2$CH$_2$—O—CH$_2$CH$_2$—O—CH$_2$CF$_3$ |
| [tetrahydrophthalimide] | Cl | F | —CH(CH$_3$)CH$_2$—O—CH$_2$CF$_3$ |
| [tetrahydrophthalimide] | Cl | F | —CH(CH$_2$F)CH$_2$—O—CH$_2$CF$_3$ |
| [tetrahydrophthalimide] | Br | F | —CH$_2$CH$_2$—O—CH(CH$_2$F)(CH$_2$F) |
| [tetrahydrophthalimide] | Cl | F | —CH$_2$CH$_2$—O—CH$_2$CF$_3$ |
| [tetrahydrophthalimide] | Cl | F | —CH(CH$_3$)CH$_2$—O—CHF$_2$ |
| [CF$_3$-tetrahydrophthalimide] | F | F | —CH$_2$CH$_2$—O—CH$_2$CH$_2$—O—CHF$_2$ |
| [CF$_3$-tetrahydrophthalimide] | H | H | —CH$_2$CH$_2$—O—CH$_2$CH$_2$—O—CH$_2$CF$_3$ |
| [CF$_3$-tetrahydrophthalimide] | Cl | F | —CH(CH$_3$)CH$_2$—O—CH$_2$CH$_2$—O—CHF$_2$ |
| [CF$_3$-tetrahydrophthalimide] | Cl | F | —CH(CH$_2$F)CH$_2$—O—CH$_2$CF$_3$ |

TABLE 1-continued

Examples of the compounds of the formula (I)

| Het | X | Y | R |
|---|---|---|---|
| 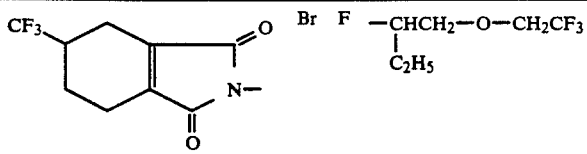 | Br | F | —CHCH$_2$—O—CH$_2$CF$_3$<br>     \|<br>     C$_2$H$_5$ |
|  | Cl | F | —CH$_2$CH$_2$—O—CH$_2$CF$_3$ |
| 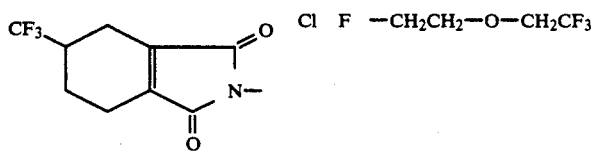 | Cl | F | —CHCH$_2$—O—CHF$_2$<br>     \|<br>     CH$_3$ |
| 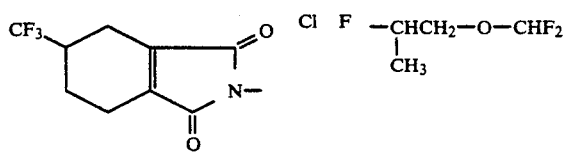 | F | F | —CH$_2$CH$_2$—O—CH$_2$CH$_2$—O—CHF$_2$ |
|  | H | H | —CH$_2$CH$_2$—O—CH$_2$CH$_2$—O—CH$_2$CF$_3$ |
| 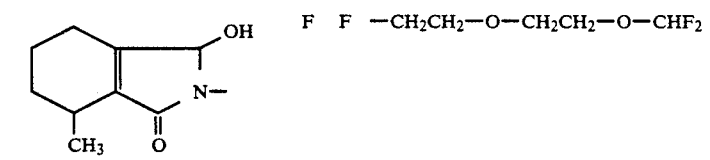 | Cl | F | —CHCH$_2$—O—CH$_2$CH$_2$—O—CHF$_2$<br>     \|<br>     CH$_3$ |
| 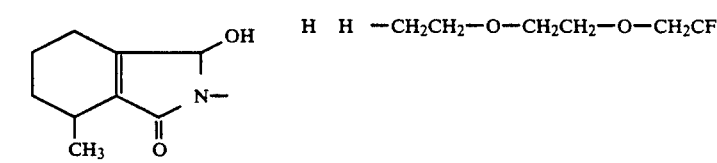 | Cl | F | —CHCH$_2$—O—CH$_2$CF$_3$<br>     \|<br>     CH$_2$F |
| 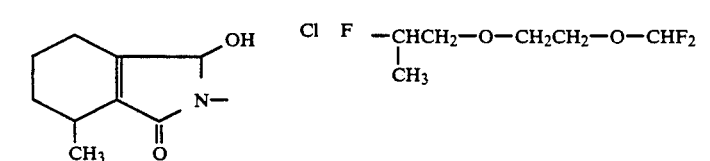 | Br | F | —CH$_2$CH$_2$—O—CH(CH$_2$F)(CH$_2$F) |
|  | Cl | F | —CH$_2$CH$_2$—O—CH$_2$CF$_3$ |
| 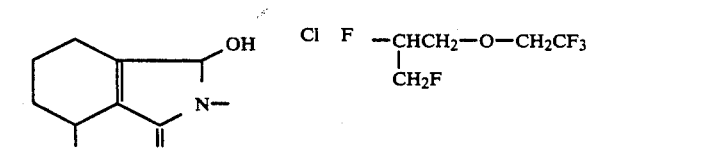 | Cl | F | —CH—CH$_2$—O—CHF$_2$<br>     \|<br>     C$_2$H$_5$ |

TABLE 1-continued

| Examples of the compounds of the formula (I) | | | |
|---|---|---|---|
| Het | X | Y | R |
| 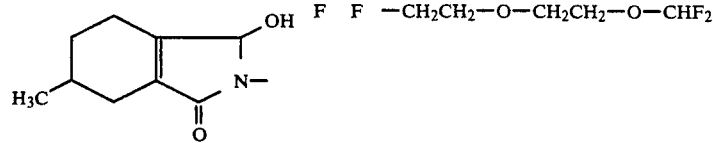 | F | F | —CH$_2$CH$_2$—O—CH$_2$CH$_2$—O—CHF$_2$ |
| 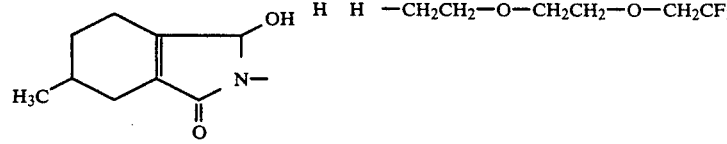 | H | H | —CH$_2$CH$_2$—O—CH$_2$CH$_2$—O—CH$_2$CF$_3$ |
| 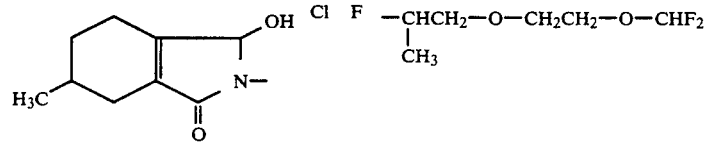 | Cl | F | —CHCH$_2$—O—CH$_2$CH$_2$—O—CHF$_2$<br>    \|<br>   CH$_3$ |
| 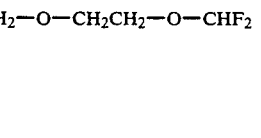 | Cl | F | —CHCH$_2$—O—CH$_2$CF$_3$<br>    \|<br>   CH$_2$F |
| 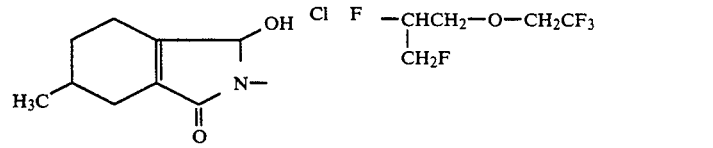 | Br | F |                CH$_2$F<br>—CH$_2$CH$_2$—O—CH<br>               CH$_2$F |
| 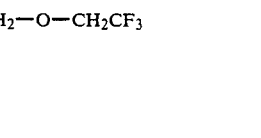 | Cl | F | —CH$_2$CH$_2$—O—CH$_2$CF$_3$ |
| 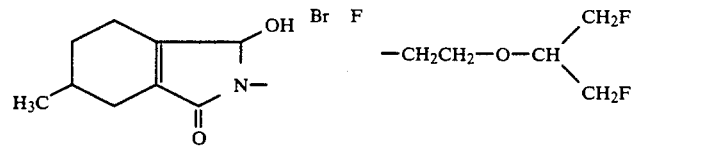 | Cl | F | —CHCH$_2$—O—CH$_2$CF$_3$<br>    \|<br>   CH$_3$ |
| 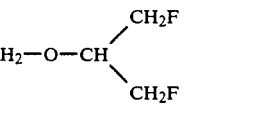 | F | F | —CH$_2$CH$_2$—O—CH$_2$CH$_2$—O—CHF$_2$ |
| 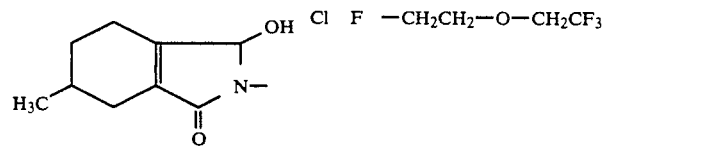 | H | H | —CH$_2$CH$_2$—O—CH$_2$CH$_2$—O—CH$_2$CF$_3$ |
| 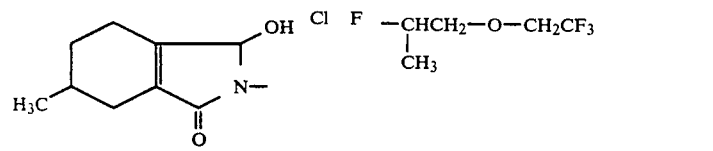 | Cl | F | —CHCH$_2$—O—CH$_2$CH$_2$—O—CHF$_2$<br>    \|<br>   CH$_3$ |

TABLE 1-continued

| Het | X | Y | R |
|---|---|---|---|
| 3-hydroxy-3a,4,7,7a-tetrahydroisoindol-1(2H)-one | Cl | F | —CH(CH₂F)CH₂—O—CH₂CF₃ |
| 3-hydroxy-3a,4,7,7a-tetrahydroisoindol-1(2H)-one | Br | F | —CH₂CH₂—O—CH(CH₂F)(CH₂F) |
| 3-hydroxy-3a,4,7,7a-tetrahydroisoindol-1(2H)-one | Cl | F | —CH₂CH₂—O—CH₂CF₃ |
| 3-hydroxy-3a,4,7,7a-tetrahydroisoindol-1(2H)-one | Cl | F | —CH(CH₃)CH₂—O—CHF₂ |
| 5-trifluoromethyl-3-hydroxy-... | F | F | —CH₂CH₂—O—CH₂CH₂—O—CHF₂ |
| 5-trifluoromethyl-3-hydroxy-... | H | H | —CH₂CH₂—O—CH₂CH₂—O—CH₂CF₃ |
| 5-trifluoromethyl-3-hydroxy-... | Cl | F | —CH(CH₃)CH₂—O—CH₂CH₂—O—CHF₂ |
| 5-trifluoromethyl-3-hydroxy-... | Cl | F | —CH(C₂H₅)CH₂—O—CH₂CF₃ |
| 5-trifluoromethyl-3-hydroxy-... | Br | F | —CH₂CH₂—O—CH(CH₂F)(CH₂F) |
| 5-trifluoromethyl-3-hydroxy-... | Cl | F | —CH₂—CH₂—O—CH₂CF₃ |

TABLE 1-continued

Examples of the compounds of the formula (I)

| Het | X | Y | R |
|---|---|---|---|
| F₃C-[cyclohexene fused pyrrolinone with OH] | Cl | F | —CHCH₂—O—CHF₂<br>    |<br>    CH₃ |
| [cyclohexene fused pyrrolinone with Cl, CH₃] | F | F | —CH₂CH₂—O—CH₂CH₂—O—CH₂CF₃ |
| [cyclohexene fused pyrrolinone with Cl, CH₃] | H | H | —CH₂CH₂—O—CH₂CH₂—O—CHF₂ |
| [cyclohexene fused pyrrolinone with Cl, CH₃] | Cl | F | —CHCH₂—O—CH₂CH₂—O—CHF₂<br>    |<br>    CH₃ |
| [cyclohexene fused pyrrolinone with Cl, CH₃] | Cl | F | —CHCH₂—O—CH₂CF₃<br>    |<br>    CH₂F |
| [cyclohexane fused pyrrolidinone with CH₃] | F | F |                 CH₂F<br>—CH₂CH₂—O—CH<br>                CH₂F |
| [cyclohexane fused pyrrolidinone with CH₃] | Cl | F | —CH₂CH₂—O—CH₂CH₂—O—CF₂CHF₂ |
| [cyclohexane fused pyrrolidinone with CH₃] | Br | F | —CH₂CH₂—O—CH₂CH₂—O—CHF₂ |
| [cyclohexene fused pyrrolinone with Cl, H₃C] | F | F | —CH₂CH₂—O—CH₂CH₂—O—CH₂CF₃ |
| [cyclohexene fused pyrrolinone with Cl, H₃C] | Cl | F | —CH₂CH₂—O—CH₂CH₂—O—CHF₂ |

TABLE 1-continued
Examples of the compounds of the formula (I)
| Het | X | Y | R |
|---|---|---|---|
| 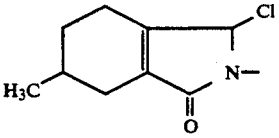 | Cl | F | —CH₂CH₂—O—CH₂CH₂—O—CH₂CF₃ |
| 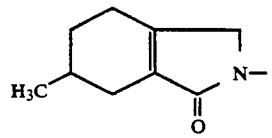 | F | F | —CHCH₂—O—CH₂CF₃<br>    |<br>    CH₃ |
| 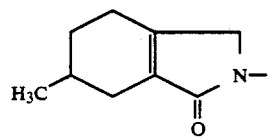 | Cl | F |                    CH₂F<br>—CH₂CH₂—O—CH<br>                   CH₂F |
| 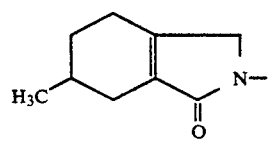 | Br | F | —CH₂CH₂—O—CH₂CH₂—O—CHF₂ |
| 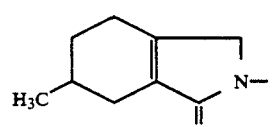 | Cl | F | —CH₂CH₂—O—CH₂CF₃ |
| 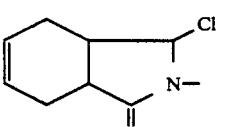 | F | F | —CH₂CH₂—O—CH₂CH₂—O—CH₂CF₃ |
| 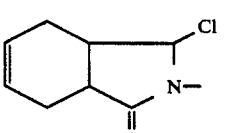 | H | H | —CHCH₂—O—CH₂CF₃<br>    |<br>    CH₂F |
| 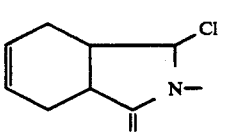 | Cl | F | —CH₂CH₂—O—CH₂CH₂—O—CHF₂ |
| 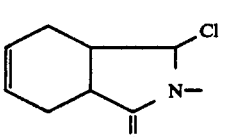 | Cl | F | —CH₂CH₂—O—CH₂CH₂—O—CH₂CF₃ |
| 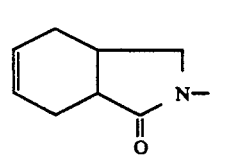 | F | F |                    CH₂F<br>—CH₂CH₂—O—CH<br>                   CH₂F |

TABLE 1-continued

Examples of the compounds of the formula (I)

| Het | X | Y | R |
|---|---|---|---|
| tetrahydroisoindolinone (with cyclohexene double bond) | Cl | F | —CHCH$_2$—O—CH$_2$CF$_3$<br>    |<br>    CH$_3$ |
| tetrahydroisoindolinone (with cyclohexene double bond) | Cl | F | —CH$_2$CH$_2$—O—CH$_2$CH$_2$—O—CF$_2$CHF$_2$ |
| 5-CF$_3$, 3-Cl tetrahydroisoindolinone | F | F | —CH$_2$CH$_2$—O—CH$_2$CH$_2$—O—CH$_2$CF$_3$ |
| 5-CF$_3$, 3-Cl tetrahydroisoindolinone | H | H | —CHCH$_2$—O—CH$_2$CF$_3$<br>    |<br>    CH$_2$F |
| 5-CF$_3$, 3-Cl tetrahydroisoindolinone | Cl | F | —CH$_2$CH$_2$—O—CH$_2$CH$_2$—O—CHF$_2$ |
| 5-CF$_3$, 3-Cl tetrahydroisoindolinone | Cl | F | —CH$_2$CH$_2$—O—CH$_2$CH$_2$—O—CH$_2$CF$_3$ |
| 5-CF$_3$ tetrahydroisoindolinone | F | F | —CH$_2$CH$_2$—O—CH(CH$_2$F)$_2$ |
| 5-CF$_3$ tetrahydroisoindolinone | Cl | F | —CHCH$_2$—O—CH$_2$CF$_3$<br>    |<br>    CH$_3$ |
| 5-CF$_3$ tetrahydroisoindolinone | Cl | F | —CH$_2$CH$_2$—O—CH$_2$CH$_2$—O—CF$_2$CHF$_2$ |
| 3-thioxo, 7-methyl hexahydroisoindolinone | F | F | —CH$_2$CH$_2$—O—CH$_2$CH$_2$—O—CHF$_2$ |

TABLE 1-continued

Examples of the compounds of the formula (I)

| Het | X | Y | R |
|---|---|---|---|
| [4-methyl-thioxo-isoindolinone] | H | H | —CHCH$_2$—O—CH$_2$CH$_2$—O—CHF$_2$<br>  \|<br>  CH$_3$ |
| [4-methyl-thioxo-isoindolinone] | Cl | F | —CH$_2$CH$_2$—O—CH$_2$CH$_2$—O—CHF$_2$ |
| [4-methyl-thioxo-isoindolinone] | Cl | F | —CH$_2$CH$_2$—O—CH$_2$CH$_2$—O—CH$_2$CF$_3$ |
| [4-methyl-thioxo-isoindolinone] | Cl | F | —CH$_2$CH$_2$—O—CH(CH$_2$F)$_2$ |
| [4-methyl-thioxo-isoindolinone] | Cl | F | —CH$_2$CH$_2$—O—CH$_2$CF$_3$ |
| [4-methyl-thioxo-isoindolinone] | Cl | F | —CHCH$_2$—O—CH$_2$CF$_3$<br>  \|<br>  CH$_2$F |
| [6-methyl-tetrahydro-thioxo-isoindolinone] | F | F | —CH$_2$CH$_2$—O—CH$_2$CH$_2$—O—CH$_2$CF$_3$ |
| [6-methyl-tetrahydro-thioxo-isoindolinone] | H | H | —CHCH$_2$—O—CH$_2$CH$_2$—O—CH$_2$CF$_3$<br>  \|<br>  CH$_3$ |
| [6-methyl-tetrahydro-thioxo-isoindolinone] | Cl | F | —CH$_2$CH$_2$—O—CH$_2$CH$_2$—O—CHF$_2$ |
| [6-methyl-tetrahydro-thioxo-isoindolinone] | Cl | F | —CH$_2$CH$_2$—O—CH$_2$CH$_2$—O—CH$_2$CF$_3$ |

TABLE 1-continued

Examples of the compounds of the formula (I)

| Het | X | Y | R |
|---|---|---|---|
| 5-methyl-3-thioxo-1-oxo-tetrahydroisoindolin-2-yl | Cl | F | —CH(CH₃)CH₂—O—CHCF₃ |
| 5-methyl-3-thioxo-1-oxo-tetrahydroisoindolin-2-yl | Cl | F | —CH₂CH₂—O—CH₂CF₃ |
| 5-methyl-3-thioxo-1-oxo-tetrahydroisoindolin-2-yl | Cl | F | —CH(CH₃)CH₂—O—CHF₂ |
| 5-methyl-1,3-dithioxo-tetrahydroisoindolin-2-yl | F | F | —CH₂CH₂—O—CH₂CH₂—O—CH₂CF₃ |
| 5-methyl-1,3-dithioxo-tetrahydroisoindolin-2-yl | H | H | —CH₂CH₂—O—CH₂CH₂—O—CH₂CF₃ |
| 5-methyl-1,3-dithioxo-tetrahydroisoindolin-2-yl | Cl | F | —CH₂CH₂—O—CH₂CH₂—O—CHF₂ |
| 5-methyl-1,3-dithioxo-tetrahydroisoindolin-2-yl | Cl | F | —CH₂CH₂—O—CH₂CH₂—O—CH₂CF₃ |
| 5-methyl-1,3-dithioxo-tetrahydroisoindolin-2-yl | Cl | F | —CH₂CH₂—O—CH(CH₂F)(CH₂F) |
| 5-methyl-1,3-dithioxo-tetrahydroisoindolin-2-yl | Cl | F | —CH₂CH₂—O—CH₂CF₃ |
| 5-methyl-1,3-dithioxo-tetrahydroisoindolin-2-yl | Cl | F | —CH(CH₃)CH₂—O—CHF₂ |

TABLE 1-continued

Examples of the compounds of the formula (I)

| Het | X | Y | R |
|---|---|---|---|
| cyclohexane-fused N-heterocycle with =S, =S, and 7-CH₃ | F | F | —CH₂CH₂—O—CH₂CH₂—O—CH₂CF₃ |
| cyclohexane-fused N-heterocycle with =S, =S, and 7-CH₃ | H | H | —CH(CH₃)CH₂—O—CH₂CH₂—O—CH₂CF₃ |
| cyclohexane-fused N-heterocycle with =S, =S, and 7-CH₃ | Cl | F | —CH₂CH₂—O—CH₂CH₂—O—CHF₂ |
| cyclohexane-fused N-heterocycle with =S, =S, and 7-CH₃ | Cl | F | —CH(CH₂F)CH₂—O—CH₂CF₃ |
| cyclohexane-fused N-heterocycle with =S, =S, and 7-CH₃ | Cl | F | —CH₂CH₂—O—CH₂CH₂—O—CH₂CF₃ |
| cyclohexane-fused N-heterocycle with =S, =S, and 7-CH₃ | Cl | F | —CH₂CH₂—O—CH₂CF₃ |
| cyclohexane-fused N-heterocycle with =S, =S, and 7-CH₃ | Cl | F | —CH₂CH₂—O—CH₂—CH(CH₂F)(CH₂F) |
| cyclohexane-fused N-heterocycle with =S, =O | F | F | —CH₂CH₂—O—CH₂CH₂—O—CH₂CF₃ |
| cyclohexane-fused N-heterocycle with =S, =O | H | H | —CH(C₂H₅)CH₂—O—CH₂CH₂—O—CH₂CF₃ |
| cyclohexane-fused N-heterocycle with =S, =O | Cl | F | —CH₂CH₂—O—CH₂CH₂—O—CHF₂ |

TABLE 1-continued
Examples of the compounds of the formula (I)
| Het | X | Y | R |
|---|---|---|---|
| 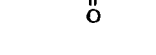 | Cl | F | —CH₂CH₂—O—CH₂CH₂—O—CH₂CF₃ |
| 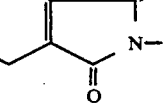 | Cl | F | —CHCH₂—O—CH₂CF₃<br>  |<br>  CH₂F |
|  | Cl | F | —CH₂CH₂—O—CH₂CF₃ |
| 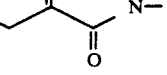 | Cl | F |                     CH₂F<br>—CH₂CH₂—O—CH₂CH⟨<br>                    CH₂F |
|  | Cl | F | —CH₂CH₂—O—CH₂CH₂—O—CHF₂ |
| 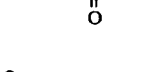 | Cl | F | —CHCH₂—O—CH₂CH₂—O—CH₂CF₃<br>  |<br>  CH₃ |
| 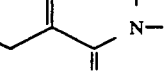 | H | H | —CHCH₂—O—CH₂CF₃<br>  |<br>  C₂H₅ |
|  | F | F | —CH₂CH₂—O—CH₂CH₂—O—CH₂CF₃ |
| 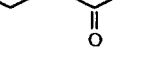 | Cl | F | —CH₂CH₂—O—CH₂CH₂—O—CHF₂ |
|  | Cl | F | —CHCH₂—O—CH₂CF₃<br>  |<br>  CH₂F |

TABLE 1-continued
Examples of the compounds of the formula (I)
| Het | X | Y | R |
|---|---|---|---|
| 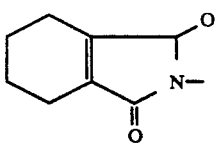 | Cl | F | —CH₂CH₂—O—CH₂CH₂—O—CF₂CHF₃ |
| 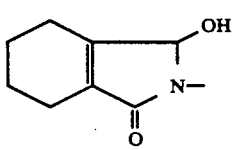 | Cl | F | —CH₂CH₂—O—CH₂CF₃ |
| 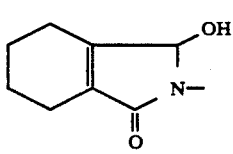 | Cl | F | —CH₂CH₂—O—CH₂CH(CH₂F)(CH₂F) |
| 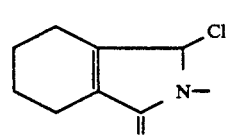 | H | H | —CH(C₂H₅)CH₂—O—CH₂CH₂—O—CH₂CF₃ |
| 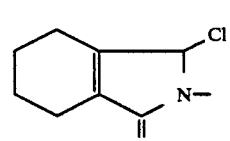 | H | H | —CH(CH₂F)CH₂—O—CH₂CF₃ |
| 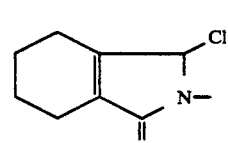 | F | F | —CH(CH₃)CH₂—O—CH₂CH₂—O—CF₂CHF₂ |
| 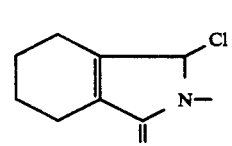 | Cl | F | —CH₂CH₂—O—CH₂CH₂—O—CHF₂ |
| 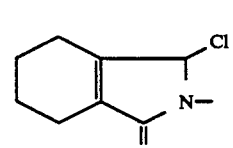 | Cl | F | —CH₂CH₂—O—CH₂CH₂—O—CH₂CF₃ |
| 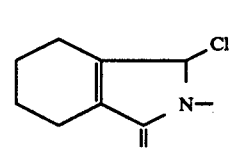 | Cl | F | —CH₂CH₂—O—CH(CH₂F)(CH₂F) |
| 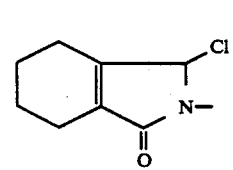 | Cl | F | —CH₂CH₂—O—CH₂CF₃ |

TABLE 1-continued

Examples of the compounds of the formula (I)

| Het | X | Y | R |
|---|---|---|---|
| 3-chloro-tetrahydroisoindolin-1-one (cyclohexene fused with N-CO ring, Cl substituent) | Cl | F | $-\underset{\underset{CH_3}{\mid}}{C}HCH_2-O-CHF_2$ |
| tetrahydroisoindolin-1-one | H | H | $-\underset{\underset{CH_3}{\mid}}{C}HCH_2-O-CH_2CH_2-O-CH_2CF_3$ |
| tetrahydroisoindolin-1-one | F | F | $-\underset{\underset{C_2H_5}{\mid}}{C}HCH_2-O-CH_2CH_2-O-CH_2CF_3$ |
| tetrahydroisoindolin-1-one | Cl | F | $-CH_2CH_2-O-CH_2CH_2-O-CHF_2$ |
| tetrahydroisoindolin-1-one | Cl | F | $-CH_2CH_2-O-CH_2CH_2-O-CH_2CF_3$ |
| tetrahydroisoindolin-1-one | Cl | F | $-CH_2CH_2-O-CH_2CF_3$ |
| tetrahydroisoindolin-1-one | Cl | F | $-\underset{\underset{CH_3}{\mid}}{C}HCH_2-O-CHF_2$ |
| hexahydroimidazo-piperidine-2,4-dione | H | H | $-\underset{\underset{CH_3}{\mid}}{C}HCH_2-O-CH_2CH_2-O-CH_2CF_3$ |
| hexahydroimidazo-piperidine-2,4-dione | H | H | $-CH_2-CH_2-O-CH\underset{\diagdown CH_2F}{\diagup CH_2F}$ |
| hexahydroimidazo-piperidine-2,4-dione | F | F | $-\underset{\underset{C_2H_5}{\mid}}{C}HCH_2-O-CH_2CH_2-O-CH_2CF_3$ |

TABLE 1-continued

Examples of the compounds of the formula (I)

| Het | X | Y | R |
|---|---|---|---|
| bicyclic hydantoin (piperidine-fused) | F | F | $-\underset{\underset{CH_3}{\mid}}{CH}CH_2-O-CH_2CH_2-O-CHF_2$ |
| bicyclic hydantoin | Cl | F | $-CH_2CH_2-O-CH_2CH_2-O-CHF_2$ |
| bicyclic hydantoin | Cl | F | $-CH_2CH_2-O-CH_2CH_2-O-CH_2CF_3$ |
| bicyclic hydantoin | Cl | F | $-\underset{\underset{CH_2F}{\mid}}{CH}CH_2-O-CH_2CF_3$ |
| bicyclic hydantoin | Cl | F | $-\underset{\underset{CH_3}{\mid}}{CH}CH_2-O-CH_2CH_2-O-CH_2CF_3$ |
| bicyclic hydantoin | Br | F | $-CH_2CH_2-O-CH\underset{\diagdown CH_2F}{\diagup CH_2F}$ |
| bicyclic hydantoin | Br | F | $-CH_2CH_2-O-CH_2CH_2-O-CHF_2$ |
| bicyclic hydantoin | Cl | F | $-CH_2CH_2-O-CH_2CF_3$ |
| bicyclic hydantoin | Cl | F | $-\underset{\underset{CH_3}{\mid}}{CH}CH_2-O-CHF_2$ |
| dimethylmaleimide | H | H | 3-hydroxy-3,4-dimethyl-pyrrolinone |

TABLE 1-continued

Examples of the compounds of the formula (I)

| Het | X | Y | R |
|---|---|---|---|
| 3,4-dimethyl-maleimide (H3C, H3C on C=C; ring: C(=O)-N-C(=O)) | F | F | -CH₂CH₂-O-CH(CH₂F)(CH₂F) |
| 3,4-dimethyl-maleimide | Cl | F | -CH₂CH₂-O-CH₂CH₂-O-CHF₂ |
| 3,4-dimethyl-maleimide | Cl | F | -CH₂CH₂-O-CH₂CH₂-O-CH₂-CF₃ |
| 3,4-dimethyl-maleimide | Cl | F | -CH₂CH₂-O-CH(CH₂F)(CH₂F) |
| 3,4-dimethyl-maleimide | Cl | F | -CH₂CH₂-O-CH₂CH₂-O-CF₂CHF₂ |
| 3,4-dimethyl-maleimide | Br | F | -CH₂CH₂-O-CH₂CH₂-O-CHF₂ |
| 3,4-dimethyl-maleimide | Br | F | -CH(CH₂F)CH₂-O-CH₂CF₃ |
| 3,4-dimethyl-maleimide | Cl | F | -CH₂CH₂-O-CH₂CF₃ |
| 3,4-dimethyl-maleimide | Cl | F | -CH(CH₃)CH₂-O-CHF₂ |
| 3,4-dimethyl-5-hydroxy-3-pyrrolin-2-one | H | H | -CH(C₂H₅)CH₂-O-CH₂CH₂-O-CH₂CF₃ |
| 3,4-dimethyl-5-hydroxy-3-pyrrolin-2-one | F | F | -CH(CH₃)CH₂-O-CH₂CH₂-O-CH₂CF₃ |

TABLE 1-continued

Examples of the compounds of the formula (I)

| Het | X | Y | R |
|---|---|---|---|
| H3C, 3-methyl-4-(methyl)-5-hydroxy-pyrrolin-2-one (OH, N-, H3C, O) | Cl | F | —CH2CH2—O—CH2CH2—O—CHF2 |
| (same Het) | Cl | F | —CH2CH2—O—CH2CH2—O—CH2CF3 |
| (same Het) | Cl | F | —CHCH2—O—CH2CF3<br>\|<br>CH2F |
| (same Het) | Cl | F | —CHCH2—O—CH2CF3<br>\|<br>CH3 |
| (same Het) | Cl | F | —CH2CH2—O—CH2CF3 |
| (same Het) | Cl | F | —CHCH2—O—CHF2<br>\|<br>CH3 |
| H3C, 3,4-dimethyl-5-chloro-pyrrolin-2-one (Cl, N-, H3C, O) | H | H | —CHCH2—O—CH2CH2—O—CHF2<br>\|<br>C2H5 |
| (same Het, Cl) | F | F | —CHCH2—O—CH2CF3<br>\|<br>CH3 |
| (same Het, Cl) | Cl | F | —CH2CH2—O—CH2CH2—O—CHF2 |
| (same Het, Cl) | Cl | F | —CH2CH2—O—CH2CH2—O—CH2CF3 |

TABLE 1-continued

Examples of the compounds of the formula (I)

| Het | X | Y | R |
|---|---|---|---|
| 3,4-dimethyl-3-pyrrolin-2-one-1-yl (3-Cl, 4-CH$_3$, 5-CH$_3$) | Cl | F | $-\underset{\underset{CH_2F}{\mid}}{CH}CH_2-O-CH_2CF_3$ |
| 3,4-dimethyl-3-pyrrolin-2-one-1-yl | H | H | $-\underset{\underset{CH_3}{\mid}}{CH}CH_2-O-CH_2CH_2-O-CH_2CF_3$ |
| 3,4-dimethyl-3-pyrrolin-2-one-1-yl | F | F | $-CH_2CH_2-O-CH_2CH_2-O-CH_2CF_3$ |
| 3,4,5,6-tetrahydrophthalimide-N-yl | Cl | F | $-CH_2-\underset{\underset{CH_3}{\mid}}{CH}-O-CH_2CF_3$ |
| 3,4,5,6-tetrahydrophthalimide-N-yl | Br | F | $-CH_2-\underset{\underset{CH_3}{\overset{CH_3}{\mid}}}{\overset{\mid}{C}}-O-CHF_2$ |
| 3,4,5,6-tetrahydrophthalimide-N-yl | H | H | $-CH_2-\underset{\underset{CH_3}{\mid}}{CH}-O-CH_2-CH_3-O-CH_2CF_3$ |
| 3,4,5,6-tetrahydrophthalimide-N-yl | Br | F | $-CH_2-\underset{\underset{CH_3}{\overset{CH_3}{\mid}}}{\overset{\mid}{C}}-O-CH_2CF_3$ |
| 3,4,5,6-tetrahydrophthalimide-N-yl | H | H | $-CH_2-\underset{\underset{CH_3}{\overset{CH_3}{\mid}}}{\overset{\mid}{C}}-O-CHF_2$ |

If, for example, 3,4,5,6-tetrahydrophthalic anhydride and 2,4-difluoro-5-(2-(2-difluoromethoxyethoxy)-ethoxy)-aniline are used as starting substances, the course of the reaction in process (a) according to the invention can be represented by the following equation:

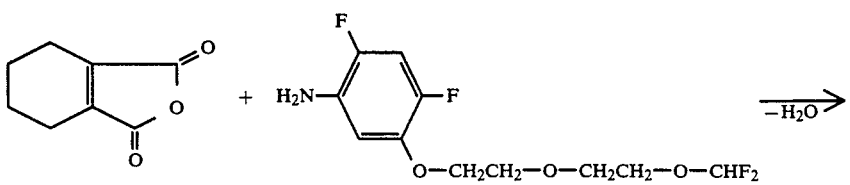

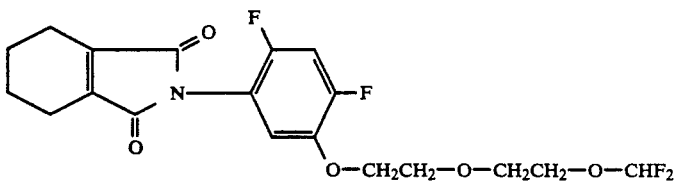

If, for example, N-(4-bromo-2-fluoro-5-(2-(2-(2,2,2-trifluoroethoxy)-ethoxy)-ethoxy)-phenyl) -dimethyl-maleimide and sodium borohydride are used as starting substances, the course of the reaction in process (b) according to the invention can be represented by the following equation:

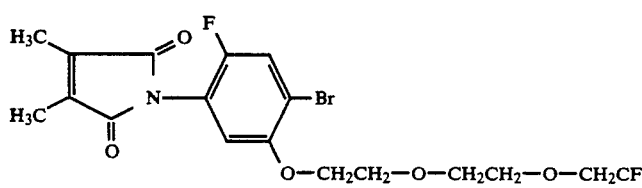

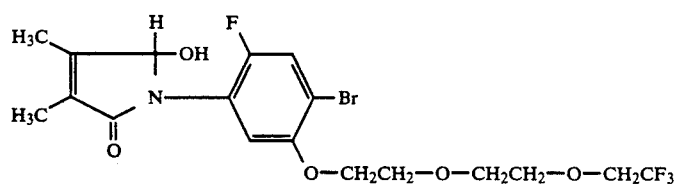

If, for example, N-(4-chloro-2-fluoro-5-(2-(2,2,2-trifluoroethoxy)-ethoxy)-phenyl)-3,4,5,6-tetrahydrophthalimide and phosphorus(V) sulphide are used as starting substances, the course of the reaction in process (c) according to the invention can be represented by the following equation:

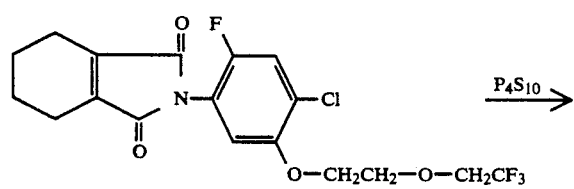

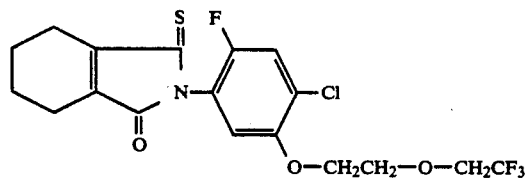

If, for example, N-(4-chloro-2-fluoro-(5-(2-difluoromethoxy-ethoxy)-phenyl)-3,4-dimethyl-Δ³-pyrrolin-5-ol-2-one and thionyl chloride are used as starting substances, the course of the reaction in process (d) according to the invention can be represented by the following equation:

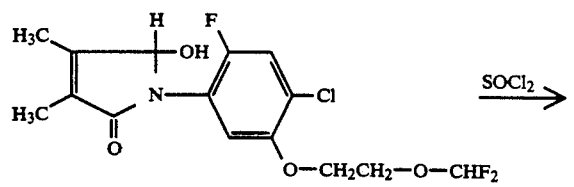

If, for example, N-(2,4-difluoro-5-(2-(1,1,2,2-tetrafluoroethoxy)-ethoxy)-phenyl)-5-chloro-3,4-dimethyl-Δ³-pyrrolin-2-one is used as the starting compound, the course of the reaction in process (e) according to the invention can be represented by the following equation:

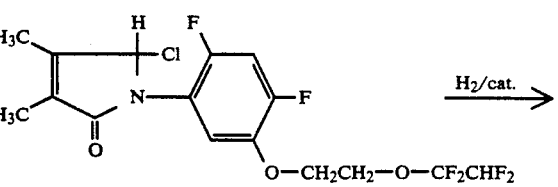

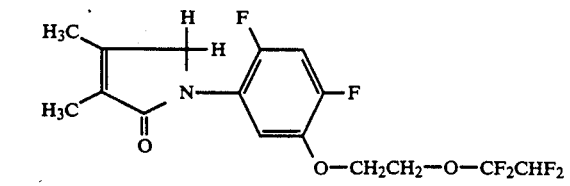

If, for example, N-(2-fluoro-5-hydroxy-phenyl)-3,4,5,6-tetrahydro-phthalimide and 2-(2-difluoromethoxy-ethoxy)-ethyl methanesulphonate are used as starting substances, the course of the reaction in process (f) according to the invention can be represented by the following equation:

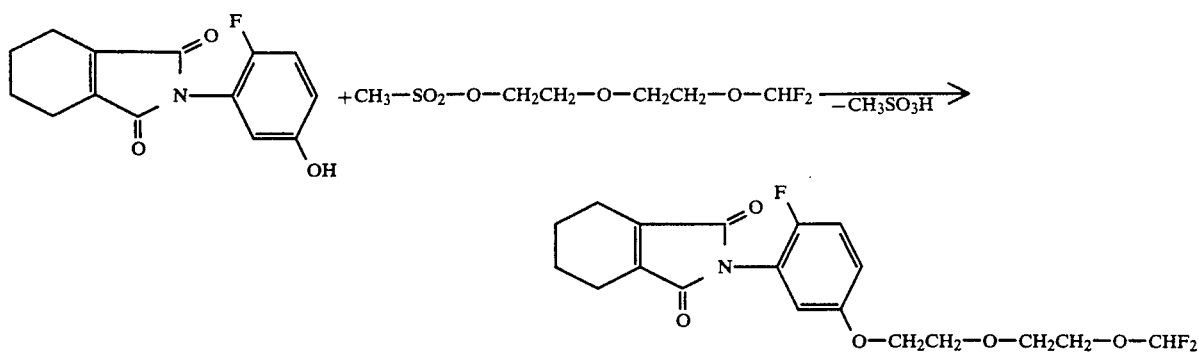

If, for example, N-(2-fluoro-5-2-(2-difluoromethoxye-thoxy)-ethoxy)-phenyl)-phthalimide and chlorine are used as starting substances, the course of the reaction in process (g) according to the invention can be represented by the following equation:

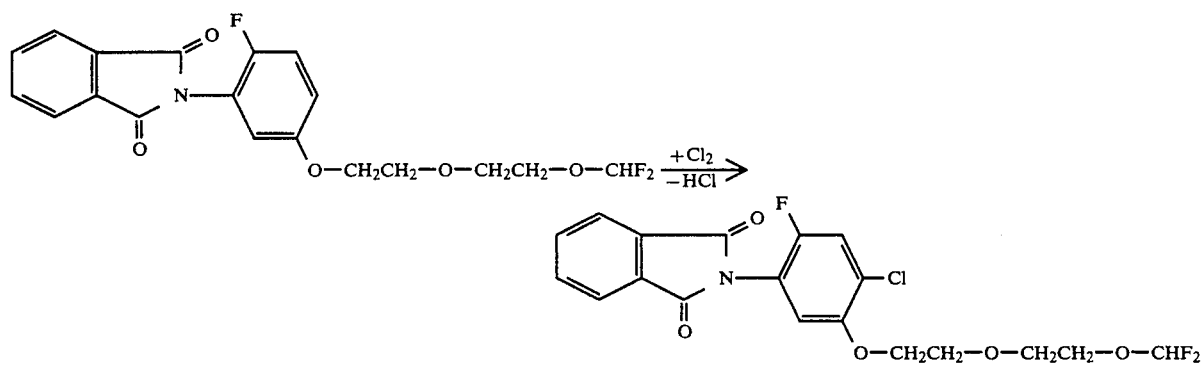

If, for example, methyl chloroformate, 4-chloro-2-fluoro-5-(2-(2-difluoromethoxy-ethoxy)-ethoxy)-aniline and ethyl piperidine-2-carboxylate are used as starting substances, the course of the reaction in process (h) according to the invention can be represented by the following equation:

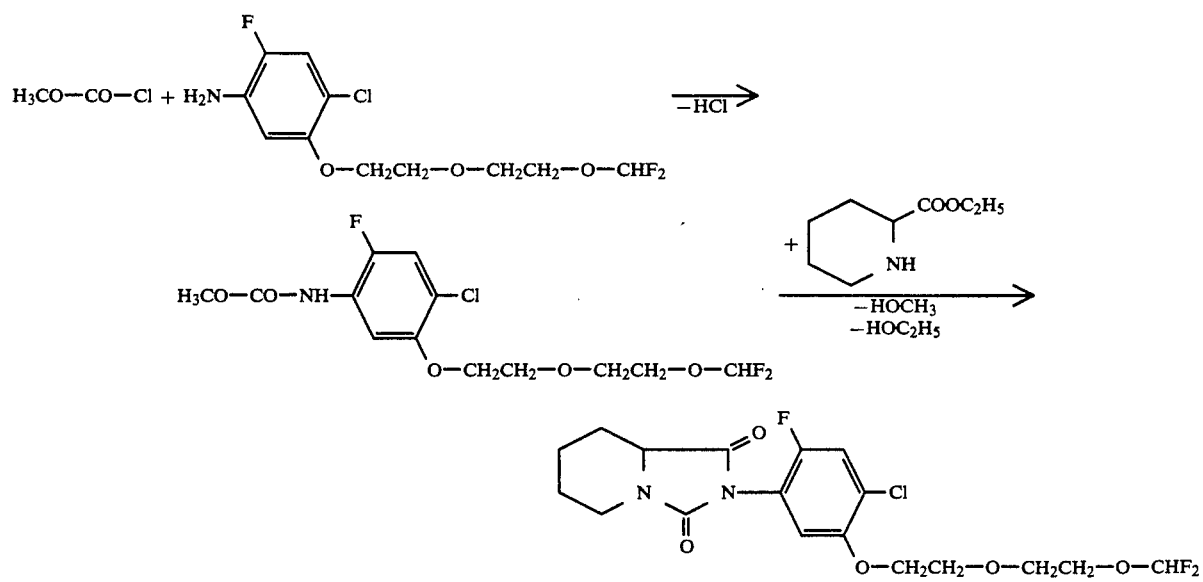

Formula (II) provides a general definition of the cyclic anhydrides to be used as starting substances for the preparation of compounds of the formula (I) in process (a) according to the invention.

In formula (II), A preferably or in particular has that meaning which has already been indicated above as preferred or as particularly preferred for A in connection with the description of the compounds of the formula (I) according to the invention.

Examples of the starting substances of the formula (II) which may be mentioned are: phthalic anhydride, 3,4,5,6-tetrahydro-phthalic anhydride, 3-methyl-, 4-methyl-, 4-trifluoromethyl- and 3,3-dimethyl-3,4,5,6-tet-rahydro-phthalic anhydride, 1,2,3,4-tetrahydro-, 1,2,3,6-tetrahydro- and 2,3,4,5-tetrahydro-phthalic anhydride, 3,6-dihydro-phthalic anhydride and dimethylmaleic anhydride.

The starting substances of the formula (II) are known chemicals for organic synthesis.

Formula (III) provides a general definition of the arylamines further to be used as starting substances for the preparation of compounds of the formula (I) in process (a) according to the invention.

In formula (III), R, X and Y preferably or in particular have those meanings which have already been indicated above as preferred or as particularly preferred for R, X and Y in connection with the description of the compounds of the formula (I) according to the invention.

Examples of the starting substances of the formula (III) which may be mentioned are: 5-(2-(2,2,2-trifluoroethoxy)-ethoxy)-, 5-(2-(2-(2,2,2-trifluoroethoxy)-ethoxy)-ethoxy)-, 5-(2-(2,2-bis-fluoromethyl-ethoxy)-ethoxy)-, 5-(1-methyl-2-(2,2,2-trifluoroethoxy)-ethoxy)-, 5-(1-ethyl-2-(2,2,2-trifluoroethoxy)-ethoxy)-, 5-(1-fluoromethyl-2-(2,2,2-trifluoroethyl)-ethoxy)-, 5-(2-difluoromethoxy-ethoxy)- and 5-(2-(2-difluoromethoxy-ethoxy)-ethoxy)-, -2-fluoro-aniline, -4-fluoro-aniline, -2,4-difluoro-aniline, -2-fluoro-4-chloro-aniline and -2-fluoro-4-bromo-aniline.

The starting substances of the formula (III) were hitherto unknown from the literature.

The new compounds of the general formula (III) are obtained when (α) hydroxyarylamines of the general formula (IX)

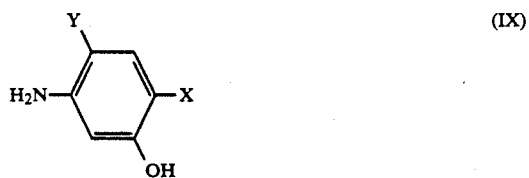
(IX)

in which

X and Y have the abovementioned meanings, are reacted with alkylating agents of the general formula (V)

X¹-R            (V)

in which

R and X¹ have the abovementioned meanings, in the presence of a diluent, such as, for example, acetone, acetonitrile, dimethylformamide, dimethyl sulphoxide or N-methyl-pyrrolidone, if appropriate in the presence of an acid acceptor, such as, for example, the carbonate, hydride or hydroxide of sodium or potassium, and if appropriate additionally in the presence of water, at temperatures between 0° C. and 100° C., or when (β) nitrophenol derivatives of the general formula (X)

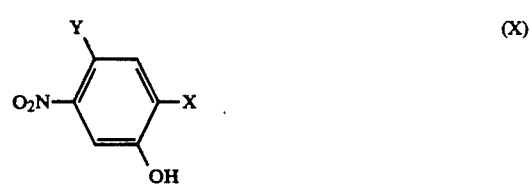
(X)

in which

X and Y have the abovementioned meanings, are reacted with alkylating agents of the general formula (V)

X¹-R            (V)

in which

R and X¹ have the abovementioned meanings, by the method indicated above under (α) and the compounds thus obtained of the general formula (XI)

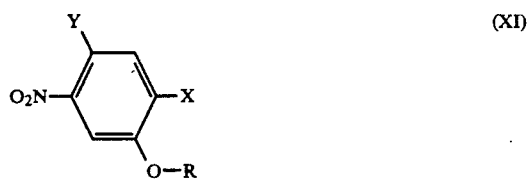
(XI)

in which

R, X and Y have the abovementioned meanings, are reduced by customary methods, for example using hydrogen in the presence of a catalyst, such as, for example, platinum on active carbon, in the presence of a diluent, such as, for example, ethanol, at temperatures between 0° C. and 100° C., or when (γ) phenol derivatives of the general formula (XII)

(XII)

in which

X and Y have the abovementioned meanings, are reacted with alkylating agents of the general formula (V)

X¹-R            (V)

in which

R and X¹ have the abovementioned meanings, by the method indicated above under (α) and the compounds thus obtained of the formula (XIII)

(XIII)

in which

R, X and Y have the abovementioned meanings, are nitrated with nitric acid to give the compounds of the formula (XI) and then reduced by customary methods (see (β)).

The nitration can be carried out in inorganic acids, such as sulphuric acid or nitric acid, but also in organic solvents, preferably halogenated hydrocarbons, such as methylene chloride, with or without addition of salts of nitrous acid, and with or without addition of urea or sulphamic acid, at temperatures from −30° C. to +60° C., preferably −10° C. to +30° C.

The phenols of the formula (XII), the hydroxyarylamines of the formula (IX) and the nitrophenol derivatives of the formula (X) required as starting substances are already known (compare EP-A 61,741).

Examples of these which may be mentioned are: 2-chloro-4-fluorophenol and 4-fluorophenol, 2-fluoro-3-hydroxy-aniline and -nitrobenzene, 4-chloro-2-fluoro-3-hydroxy-aniline and -nitrobenzene and 4-bromo-2-fluoro- 3-hydroxy-aniline and -nitrobenzene.

Formula (V) provides a general definition of the alkylating agents further required as starting substances.

In formula (V), R preferably or in particular has that meaning which has already been indicated above as preferred or as particularly preferred for R in connection with the description of the compounds of the formula (I) according to the invention and X: preferably represents chlorine, bromine, methylsulphonyloxy, phenylsulphonyloxy or tolylsulphonyloxy.

Examples of the starting substances of the formula (V) which may be mentioned are: 2-(2,2,2-trifluoroethoxy)-ethyl, 2-(2-(2,2,2-trifluoroethoxy)-ethoxy)-ethyl, 2-(2,2-bis-fluoromethyl-ethoxy)-ethyl, 2-(2,2,2-trifluoroethoxy)-1-methyl-ethyl, 2-(2,2,2-trifluoroethoxy)-1-ethyl-ethyl, 1-fluoromethyl-2-(2,2,2-trifluoroethoxy)-ethyl, 2-difluoromethoxy-ethyl and 2-(2-difluoromethoxy-ethoxy)-ethyl chloride and bromide; in addition ethyl 2-(2,2,2-trifluoroethoxy) ethyl, 2-(2-(2,2,2-trifluoroethoxy)-ethoxy)-ethyl, 2-(2,2-bis-fluoromethyl-ethoxy)-ethyl, 2-(2,2,2-trifluoroethoxy)-1-methyl-ethyl,2-(2,2,2-trifluoroethoxy)-1-ethyl, 1-fluoromethyl-2-(2,2,2-trifluoroethoxy) ethyl, 2-di-fluoromethoxy-ethyl and 2-(2-difluoromethoxy-ethoxy), methanesulphonate, benzenesulphonate and p-toluenesulphonate.

The starting substances of the formula (V) were hitherto unknown from the literature.

The new compounds of the formula (V) are obtained, for example, when corresponding alcohols of the formula (XIV)

$$\text{HO-R} \qquad \text{(XIV)}$$

in which
R has the abovementioned meaning,
α) are reacted in the case in which $X^1$ represents chlorine or bromine with a chlorinating agent, such as, for example, thionyl chloride, phosphorus(III) chloride, phosphorus(V) chloride and/or phosphoryl chloride, or with a brominating agent such as, for example, phosphorus(III) bromide, if appropriate in the presence of a basic compound such as, for example, pyridine and if appropriate in the presence of a diluent, such as, for example, diethyl ether, at temperatures between −10° C. and +120° C., or β) are reacted in the case in which $X^1$ represents methylsulphonyloxy, phenylsulphonyloxy or tolylsulphonyloxy with methanesulphonyl chloride, benzenesulphonyl chloride or toluenesulphonyl chloride, if appropriate in the presence of a basic compound, such as, for example, pyridine, and if appropriate in the presence of a diluent, such as, for example, methylene chloride, at temperatures between −20° C. and +60° C.

Formula (XIV) provides a general definition of the alcohols required as intermediates. In formula (XIV), R preferably or in particular has that meaning which has already been indicated above as preferred or as particularly preferred for R in connection with the description of the compounds of the formula (I) according to the invention.

Examples of the intermediates of the formula (XIV) which may be mentioned are: 2-(2,2,2-trifluoroethoxy)-ethanol, 2-(2-(2,2,2-trifluoro-ethoxy)-ethoxy)-ethanol, 2-(2,2-bis-fluoromethyl-ethoxy)-ethanol, 2-(2,2-trifluoroethoxy)-1-methyl-ethanol, 2-(2,2,2-trifluoroethoxy)-1-ethyl-ethanol, 1-fluoromethyl-2-(2,2,2-trifluoroethoxy)-ethanol, 2-(2-difluoromethoxyethoxy)-ethanol and 2-difluoromethoxy-ethanol.

Some of the alcohols of the formula (XIV) are known (compare J. Am. Chem. Soc. 79 (1957); U.S. Pat. No. 3,394,115).

The alcohols of the formula (XIV), in which R represents alkyl which is branched, interrupted by at least one oxygen atom and substituted by at least one fluorine atom, are new.

The new alcohols of the formula (XIV) are preferred, in which R represents branched oxaalkyl or dioxaalkyl having up to 10 carbon atoms and substituted by 2 to 4 fluorine atoms. The new alcohols are indicated in the following by the formula (XIVa).

Examples of the new compounds of the formula (XIV) which may be mentioned are: 1-methyl-2-(2,2,2-trifluoroethoxy)-ethanol, 1-ethyl-2-(2,2,2-trifluoroethoxy)-ethanol, 1-fluoromethyl-2-(2,2,2-trifluoroethoxy)-ethanol and 2-(2-fluoro-1-fluoromethylethoxy)-ethanol.

The new compounds of the formula (XIVa) are obtained when suitable alcohols, such as, for example, 2-fluoro-1-fluoromethylethanol (1,3-difluoro-2-propanol) or 2,2,2-trifluoroethanol are reacted with suitable oxiranes, such as, for example, ethylene oxide, propylene oxide, butylene oxide or epifluorohydrin, in the presence of bases, such as, for example, sodium or potassium hydroxide, at temperatures between −80° C. and +120° C. and at pressures between 1,000 hPa and 10,000 hPa (compare Preparation Examples).

Formula (Ia) provides a general definition of the substituted arylimides to be used as starting substances in processes (b) and (c) according to the invention for the preparation of compounds of the formula (I).

In formula (Ia), A, R, X and Y preferably or in particular have those meanings which have already been indicated above as preferred or as particularly preferred for A, R, X and Y in connection with the description of the compounds of the formula (I) according to the invention.

Examples of the starting substances of the formula (Ia) are to be inferred from Table 1 (above).

The substituted arylimides of the formula (Ia) are new compounds according to the invention; they can be prepared by process (a) according to the invention.

Formula (Ib) provides a general definition of the N-aryl nitrogen heterocycles to be used as starting substances in process (d) according to the invention for the preparation of compounds of the formula (I).

In formula (Ib), A, R, X and Y preferably or in particular have those meanings which have already been indicated above as preferred or as particularly preferred for A, R, X and Y in connection with the description of the compounds of the formula (I) according to the invention.

Examples of the starting substances of the formula (Ib) are to be inferred from Table 1 (above).

The N-aryl nitrogen heterocycles of the formula (Ib) are new compounds according to the invention; they can be prepared by process (b) according to the invention.

Formula (Ic) provides a general definition of the N-aryl nitrogen heterocycles to be used as starting substances for the preparation of compounds of the formula (I) in process (e) according to the invention.

In formula (Ic), A, R, X and Y preferably or in particular have those meanings which have already been mentioned above as preferred or as particularly preferred for A, R, X and Y in connection with the description of the compounds of the formula (I) according to the invention.

Examples of the starting substances of the formula (Ic) are to be inferred from Table 1 (above).

The N-aryl nitrogen heterocycles of the formula (Ic) are new compounds according to the invention. They can be prepared by process (d) according to the invention.

Formula (IV) provides a general definition of the hydroxyarylimides to be used as starting substances for the preparation of compounds of the formula (I) in process (f) according to the invention.

In the formula (IV), A, X and Y preferably or in particular have those meanings which have already been mentioned above as preferred or as particularly preferred for A, X and Y in connection with the description of the compounds of the formula (I) according to the invention.

Examples of the starting substances of the formula (IV) which may be mentioned are: N-(2-fluoro-5-hydroxy-phenyl)-, N-(2,4-difluoro-5-hydroxy-phenyl)-, N-(4-chloro-2-fluoro-5-hydroxy-phenyl)-phthalimide, N-(2-fluoro-5-hydroxy-phenyl)-, N-(2,4-difluoro-5-hydroxy-phenyl)-, N-(4-chloro-2-fluoro-5-hydroxy-phenyl)- and N-(4-bromo-2-fluoro-5-hydroxyphenyl)-3,4,5,6-tetrahydrophthalimide, N-(2-fluoro-5-hydroxy-phenyl)-, N-(2,4-difluoro-5-hydroxy-phenyl)-, N-(4-chloro-2-fluoro-5-hydroxy-phenyl)- and N-(2-fluoro-4-bromo-5-hydroxy-phenyl)-, -3-methyl-, -4-methyl-, -4-trifluoromethyl- and -3,3-dimethyl-3,4,5,6-tetrahydrophthalimide,N-(2-fluoro-5-hydroxy-phenyl)-,N-(2,4-difluoro-5-hydroxy-phenyl)-, N-(4-chloro-2-fluoro-3-hydroxy-phenyl)- and N-(4-bromo-2-fluoro-5-hydroxy-phenyl)-3,6-dihydro-phthalimide and N-(2-fluoro-5-hydroxy-phenyl-), N-(2,4-difluoro-5-hydroxy-phenyl-,N-(4-chloro-2-fluoro-5-hydroxy-phenyl)- and N-(4-bromo-2-fluoro-5-hydroxy-phenyl)-dimethylmaleimide.

The starting substances of the formula (IV) are known and/or can be prepared by processes which are known per se (compare EP-A 61,741).

Formula (V) provides a general definition of the alkylating agents further to be used as starting substances for the preparation of compounds of the formula (I) in process (f) according to the invention.

In formula (V), R preferably or in particular has that meaning which has already been indicated above as preferred or as particularly preferred for R in connection with the description of the compounds of the formula (I) according to the invention and X: preferably represents chlorine, bromine, iodine, methylsulphonyl, phenylsulphonyl or tolylsulphonyl.

Examples of the starting substances of the formula (V) have already been mentioned above in connection with the description of the starting substances for process (a) according to the invention.

Formula (Id) provides the general definition of the substituted arylimides to be used as starting substances for the preparation of compounds of the formula (I) in process (g) according to the invention.

In formula (Id), A, R and Y preferably or in particular have those meanings which have already been indicated above as preferred or as particularly preferred for A, R and Y in connection with the description of the compounds of the formula (I) according to the invention.

Examples of the starting substances of the formula (Id) are to be inferred from Table 1 (above).

The substituted arylimides of the formula (Id) are new compounds according to the invention, and they can be prepared by process (a) according to the invention.

Formula (III) provides a general definition of the arylamines to be used as starting materials for the preparation of compounds of the formula (I) in process (h) according to the invention.

In formula (III), R, X and Y preferably or in particular have those meanings which have already been mentioned above as preferred or as particularly preferred for R, X and Y in connection with the description of the compounds of the formula I according to the invention.

Examples of the starting substances of the formula (III) and processes for their preparation have already been indicated above in connection with the description of the starting substances for process (a) according to the invention.

Formula (VI) provides a general definition of the chloroformates further to be used as starting substances in process (h) according to the invention. In this formula (VI), $R^3$ preferably represents methyl, benzyl or phenyl.

Examples of the starting substances of the formula (VI) which may be mentioned are: methyl, benzyl and phenyl chloroformate.

The chloroformates of the formula (VI) are known chemicals for organic synthesis.

Formula (VIII) provides a general definition of the piperidine-2-carboxylates further to be used as starting substances in process (h) according to the invention.

In formula (VIII), $R^1$ and $R^2$ preferably or in particular have those meanings which have already been indicated above as preferred or as particularly preferred for $R^1$ and $R^2$ in connection with the description of the compounds of the formula (I) according to the invention and $R^4$ preferably represents methyl or ethyl.

Examples of the starting substances of the formula (VIII) which may be mentioned are: methyl and ethyl piperidine-2-carboxylate.

The starting substances of the formula (VIII) are known chemicals for organic synthesis.

Process (a) according to the invention for the preparation of the new compounds of the formula (I) is preferably carried out using diluents. Suitable diluents here are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, carboxylic acids such as formic acid, acetic acid or propionic acid, esters such as methyl acetate and ethyl acetate, nitriles such as, for example, acetonitrile and propionitrile, amides such as, for example, dimethylformamide, dimethylacetamide and N-methyl-pyrrolidone and also dimethyl sulphoxide, tetramethylene sulphone and hexamethylphosphoramide.

Process (a) according to the invention can optionally be carried out in the presence of a suitable reaction auxiliary. Inorganic or organic acids such as, for example, acetic acid or p-toluenesulphonic acid, anhydrides such as, for example, acetic anhydride or acid chlorides such as acetyl chloride are preferably used as reaction auxiliaries. It is also possible to use other customary dehydrating agents such as, for example, N,N'-dicyclohexylcarbodiimide or customary acylating catalysts, such as, for example, 4-(N,N-dimethylamino)pyridine as reaction auxiliaries.

The reaction temperatures can be varied within a relatively large range when carrying out process (a) according to the invention. In general the reaction is carried out at temperatures between 20° C. and 180° C., preferably at temperatures between 50° C. and 150° C.

For carrying out process (a) according to the invention, 1.0 to 1.5 moles, preferably 1.0 to 1.2 moles of amine of the formula (III) and, if appropriate, 0.01 to 1.2 moles, preferably 0.1 to 1.0 mole of reaction auxiliary are in general employed per mole of anhydride of the formula (II). The reaction is carried out, and the reaction products are worked up and isolated by generally customary methods (also compare the Preparation Examples).

Suitable reducing agents for carrying out process (b) according to the invention are all reducing agents which can customarily be used for reduction reactions of this type. Complex hydrides, such as, for example, sodium borohydride, sodium cyanoborohydride, lithium borohydride or lithium hydride are preferably used.

Suitable diluents for carrying out process (b) according to the invention are, depending on the reducing agent used, all customary organic or inorganic solvents. Ethers, such as diethyl ether, dioxane or tetrahydrofuran or alcohols, such as methanol, ethanol or propanol are preferably used.

The reaction temperatures can be varied within a relatively large range when carrying out process (b) according to the invention, depending on the reducing agent used. In general, the reaction is carried out at temperatures between −20° C. and +150° C., preferably at temperatures between 0° C. and 120° C.

For carrying out process (b) according to the invention, 0.1 to 2.0 moles, preferably 0.25 to 1.5 moles of reducing agent are in general employed per mole of substituted arylimide of the formula (Ia). The reaction is carried out, and the reaction products are worked up and isolated by generally customary methods.

Suitable sulphurizing agents for carrying out process (c) according to the invention are all sulphurizing agents customarily utilizable for sulphurization reactions of this type. Phosphorus-sulphur compounds, such as, for example, phosphorus(V) sulphide ($P_4S_{10}$) or the so-called Lawesson reagent (2,4-bis-(4-methoxyphenyl)-1,3-dithia-phosphetane-2,4-disulphide are preferably used.

Suitable diluents for carrying out process (c) according to the invention are inert organic solvents. These particularly include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl or ethylene glycol diethyl ether.

The reaction temperatures can be varied within a relatively large range when carrying out process (c) according to the invention. In general, the reaction is carried out at temperatures between 0° C. and 180° C., preferably at temperatures between 20° C. and 150° C.

For carrying out process (c) according to the invention, between 0.2 and 2.0 moles, preferably between 0.5 and 1.5 moles, of sulphurizing agent are in general employed per mole of arylimide of the formula (Ia).

The reaction is carried out, and the reaction products are worked up and isolated by a procedure which is known per se (compare Bull. Soc. Chim. Belg. 87 (1978), 223–228). In general, mixtures of singly and doubly sulphurized products are obtained here, which can be separated by customary separation methods (for example chromatography or crystallization).

Suitable diluents for carrying out process (d) according to the invention are inert organic solvents. These particularly include aliphatic, alicyclic or aromatic, optionally halogenated hydrocarbons, such as, for example, benzine, benzene, toluene, xylene, chlorobenzene, benzene, petroleum ether, hexane, cyclohexane, dichloromethane petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether or nitriles such as acetonitrile or propionitrile.

Process (d) according to the invention can optionally be carried out in the presence of a suitable reaction auxiliary. Those which are suitable are in particular organic amines or amides. Pyridine, dimethylaniline or dimethylformamide are preferably used.

The reaction temperatures can be varied within a relatively large range when carrying out process (d) according to the invention. In general, the reaction is carried out at temperatures between 0° C. and 120° C., preferably at temperatures between 20° C. and 80° C.

For carrying out process (d) according to the invention, 1.0 to 5.0 moles, preferably 1.0 to 2.0 moles of thionyl chloride and, if appropriate, 0.1 to 2.0 moles, preferably 0.5 to 1.5 moles, of reaction auxiliary are in general employed per mole of N-aryl nitrogen heterocycle of the formula (Ib).

The reaction is carried out, and the reaction products are worked up and isolated by generally customary methods.

Suitable catalysts for carrying out process (e) according to the invention are all customary hydrogenation catalysts. Noble metal catalysts, such as, for example, platinum, platinum oxide, palladium or ruthenium, if appropriate on a suitable support such as, for example, carbon or silica, are preferably used.

Suitable diluents for carrying out process (e) according to the invention are inert organic solvents. These in particular include aliphatic or alicyclic, optionally halogenated hydrocarbons, such as, for example, benzine, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether or alcohols such as methanol, ethanol or propanol.

Process (e) according to the invention can optionally be carried out in the presence of a suitable acid-binding agent. Alkali metal carbonates such as sodium carbonate or potassium carbonate or organic bases such as pyridine or lutidine are preferably used.

The reaction temperatures can be varied within a relatively large range when carrying out process (e) according to the invention. In general the reaction is carried out at temperatures between −20° C. and 100° C., preferably at temperatures between 0° C. and 50° C.

The process according to the invention can be carried out at normal pressure or at elevated pressure. The reaction is preferably carried out under normal pressure.

For carrying out process (e) according to the invention, 1.0 to 3.0 moles, preferably 1.0 to 1.5 moles, of hydrogen and if appropriate 1.0 to 3.0 moles, preferably 1.0 to 1.5 moles, of acid-binding agent are in general employed per mole of N-aryl nitrogen heterocycle of the formula (Ic). The reaction is carried out, and the reaction products are worked up and isolated by generally customary methods.

Process (f) according to the invention for the preparation of the new compounds of the formula (I) is preferably carried out using diluents. Suitable diluents here are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidine and also dimethyl sulphoxide, tetramethylene sulphone and hexamethylphosphoramide.

Acid acceptors which can be employed in process (f) according to the invention are all acid-binding agents customarily utilizable for reactions of this type. Alkali metal hydroxides such as, for example, sodium hydroxide and potassium hydroxide, alkaline earth metal hydroxides such as, for example, calcium hydroxide, alkali metal carbonates and alkoxides such as sodium carbonate and potassium carbonate, sodium tert-butoxide and potassium tert-butoxide, and in addition aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5.4.0]-undec-7-ene (DBU) and 1,4-diazabicyclo[2.2.2]-octane (DABCO) are preferred.

The reaction temperatures can be varied within a relatively large range in process (f) according to the invention. In general, the reaction is carried out at temperatures between 0° C. and 150° C., preferably at temperatures between 10° C. and 100° C.

Process (f) according to the invention is generally carried out at normal pressure.

For carrying out process (f) according to the invention, between 1 and 2 moles, preferably between 1.1 and 1.5 moles, of alkylating agent of the formula (V) are in general employed per mole of hydroxyarylimide of the formula (IV).

The reaction is carried out, and the reaction products are worked up and isolated by generally customary methods.

Suitable halogenating agents for carrying out process (g) according to the invention are all halogenating agents customarily utilizable for the halogenation of aromatic compounds. Elemental halogens, such as chlorine or bromine, or halogen compounds, such as sulphuryl chloride, are preferably used.

Process (g) is optionally carried out using catalysts. Those which are suitable are preferably acidic or electrophilic halogen compounds, such as, for example, hydrogen chloride, hydrogen bromide, aluminum chloride, aluminum bromide, iron(III) chloride or iron(III) bromide.

Process (g) according to the invention is preferably carried out using diluents. Suitable organic solvents are above all those which have already been indicated above for process (f), but in addition also acetic acid and/or water.

The reaction temperatures can be varied within a relatively large range in process (g) according to the invention. In general, the reaction is carried out at temperatures between 0° C. and 150° C., preferably at temperatures between 20° C. and 120° C.

Process (g) is in general carried out at normal pressure.

For carrying out process (g) according to the invention, between 1 and 5 moles, preferably between 1 and 3 moles, of halogenating agent are in general employed per mole of starting compound of the formula (Id).

The reaction is carried out, and the reaction products are worked up and isolated by generally customary methods.

Process (h) according to the invention is preferably carried out using diluents. Suitable organic solvents are above all those which have already been indicated above for process (f), and in the second step in addition preferably also alcohols, such as methanol, ethanol or isopropanol.

Process (h) according to the invention is preferably carried out in the presence of an acid acceptor. Those which are predominantly suitable are those acidbinding agents which have already been indicated above for process (f).

The reaction temperatures can be varied within a relatively large range in process (h) according to the invention. In general, the reaction is carried out at temperatures between −20° C. and +150° C., preferably at temperatures between 0° C. and 100° C.

Process (h) according to the invention is in general carried out at normal pressure.

For carrying out process (h) according to the invention, between 0.8 and 1.5 moles, preferably between 1.0 and 1.2 moles, of chloroformates of the formula (VI) are in general employed per mole of arylamine of the formula (III) and between 0.8 and 1.5 moles, preferably between 1.0 and 1.2 moles, of piperidine-2-carboxylate of the formula (VIII) are in general employed per mole of arylurethane of the formula (VII).

The reaction is carried out, and the reaction products are worked up and isolated by generally customary methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are particularly suitable for selectively combating dicotyledon weeds in monocotyledon cultures both in the pre-emergence and in the post-emergence method.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

The amount of leaves on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted into the customary formulations, such as solutions, emulsions, wettable powders, suspensions, powders, dusting agents, pastes, soluble powders, granules, suspension emulsion concentrates, natural and synthetic materials impregnated with active compound and very fine capsules in polymeric substances.

These formulations are produced in a known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

When used as herbicides, the active compounds according to the invention, as such or in the form of their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for controlling weeds in cereals; 4-amino-3-methyl-6-phenyl-1,2,4-triazin-5(4H)-one (METAMITRON) for controlling weeds in sugar beets, and 4-amino-6-(1,1-dimethylethyl)-3-methylthio-1,2,4-triazin-5(4H)-one (METRIBUZIN) for controlling weeds in soy beans; in addition also 2,4-dichlorophenoxyacetic acid (2,4-D); 4(2,4-dichlorophenoxy)-butyric acid (2,4-DB); 2,4-di-chlorophenoxypropionic acid (2,4-DP); 3-isopropyl-2,1,3-benzothiadiazin-4-one-2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); 2-chloro-N-(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); 2-[4-(2,4-dichlorophenoxy)-(phenoxy]-propionic acid, its methyl or its ethyl ester (DICLOFOP); 4-amino-6-t-butyl-3-ethylthio-1,2,4-triazin-5(4H)-one (ETHIOZIN);2-{4-[(6-chloro-2-benzoxazolyl)-oxy]-phenoxy}-propanoic acid, its methyl or its ethyl ester (FENOXAPROP); [(4-amino-3,5-dichloro-6-fluoro-2-pyridinyl)-oxy]-acetic acid or its 1methylheptyl ester (FLUROXYPYR); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)acetanilide (MEFENACET); 2-{[[((4-methoxy-6-methyl-1,3,5-triazin-2-yl)-amino)-carbonyl]-amino]-sulphonyl}-benzoic acid or its methyl ester (METSULFURON); N-(1-ethylpropyl)-3,4-dimethyl-2,6-dinitroaniline (PENDIMETHALIN); 0-(6-chloro-3-phenyl-pyridazin-4-yl) S-octyl-thiocarbonate (PYRIDATE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]amino]-sulphonyl]-thiophene-2-carboxylate (THIAMETURON); S-(2,3,3-trichlorallyl) N,N-diisopropyl thiolcarbamate (TRIALLATE). Some mixtures surprisingly also exhibit a synergistic effect.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5.0 kg per ha.

The preparation and the use of the active compounds according to the invention can be seen from the following examples.

PREPARATION EXAMPLES

Example 1

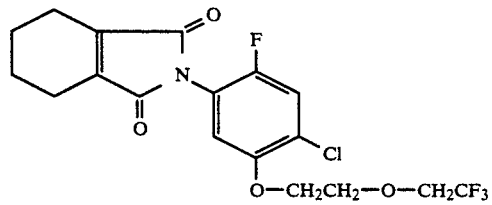

(Process (a))

3.5 g (0.012 mol) of 4-chloro-2-fluoro-5-(2-(2,2,2-trifluoroethoxy)-ethoxy)-aniline, 1.85 g (0.012 mol) of 3,4,5,6-tetrahydrophthalic anhydride and 0.15 g (0.0012 mol) of 4-N,N-dimethylaminopyridine are dissolved in 20 ml of glacial acetic acid and heated for 3.5 hours at 90°60 C. After cooling, the reaction mixture is discharged into 100 ml of water and the resulting precipitate is extracted with dichloromethane. The organic phase is washed successively with saturated sodium hydrogencarbonate solution and saturated sodium chloride solution, dried over magnesium sulphate and freed from solvent in vacuo. 4.8 g (93.5% of theory) of 4-chloro-2-fluoro-5-(2-(2,2,2-trifluoroethoxy)-ethoxy-1-(3,4,5,6-tetrahydrophthalimide)-phenyl of melting point 45° C. to 47° C. are obtained as a residue.

The compounds of the formula (I) shown in Table 2 below can be obtained analogously to Example 1 and/or in accordance with the general description of the preparation process according to the invention.

TABLE 2

Examples of the compounds of the formula (I)

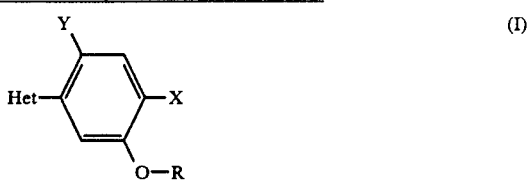

(I)

| Example No. | Het | X | Y | R | Physical data |
|---|---|---|---|---|---|
| 2 | 3,4-dimethyl-maleimide-N-yl (H₃C, H₃C on maleimide with N) | Cl | F | $-CH_2CH_2-O-CH_2CF_3$ | m.p. 75–77° C. |
| 3 | hexahydrophthalimide-N-yl | Cl | F | $-CH_2CH_2-O-CH(CH_2F)_2$ | 6.83[a] |
| 4 | hexahydrophthalimide-N-yl | Cl | F | $-CH(CH_3)CH_2-O-CH_2CF_3$ | 6.89[a] |
| 5 | hexahydrophthalimide-N-yl | Cl | F | $-CH(C_2H_5)CH_2-O-CH_2CF_3$ | 6.92[a] |
| 6 | hexahydrophthalimide-N-yl | Cl | F | $-CH(CH_2F)CH_2-O-CH_2CF_3$ | 7.00[a] |
| 7 | hexahydrophthalimide-N-yl | Cl | F | $-CH_2CH_2OCH_2CH_2O-CH_2CF_3$ | 6.85[a] |

[a] $^1$H-NMR (CDCl₃, δ, ppm): in each case a doublet (J = 6.5 Hz) for

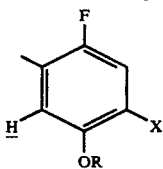

STARTING SUBSTANCES OF THE FORMULA (III)

Example (III-1):

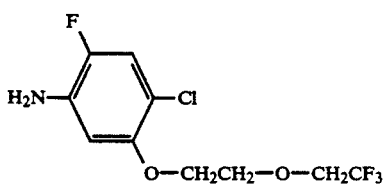

2.8 g (0.05 mol) of potassium hydroxide, dissolved in 3.5 ml of water, are added to a solution of 5.5 g (0.034 mol) of 4-chloro-2-fluoro-5-hydroxyaniline in 80 ml of N-methylpyrrolidone. The mixture is stirred for 15 minutes and 7.0 g (0.034 mol) of 2-(2,2,2-trifluoroethoxy)-ethyl bromide are then added. The reaction mixture is stirred for 16 hours at room temperature and then discharged into 200 ml of water.

The precipitated oil is extracted using dichloromethane, and the organic phase is washed twice with water, dried over magnesium sulphate and freed from solvent in vacuo. 8.2 g (84.4 % of theory) of 4-chloro-2-fluoro-5-(2(2,2,2-trifluoroethoxy)-ethoxy)-aniline are obtained as a brown oil. $^1$H-NMR(CDCl$_3$, δ): 6.38 ppm (d, J=8.03 Hz)

The compounds of the formula (III) shown in Table 3 below can be prepared analogously.

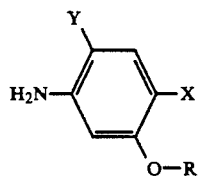

(III)

TABLE 3

| Example No. | X | Y | R | Physical data |
|---|---|---|---|---|
| III-2 | Cl | F | —CH$_2$CH$_2$—O—CH$_2$CH$_2$—O—CH$_2$CF$_3$ | 6.42$^{(a)}$ |
| III-3 | Cl | F | —CH$_2$CH$_2$—O—CH(CH$_2$F)(CH$_2$F) | 6.40$^{(a)}$ |

TABLE 3-continued

| Example No. | X | Y | R | Physical data |
|---|---|---|---|---|
| III-4 | Cl | F | —CHCH$_2$—O—CH$_2$CF$_3$ (C$_2$H$_5$) | 6.49$^{(a)}$ |
| III-5 | Cl | F | —CHCH$_2$—O—CH$_2$CF$_3$ (CH$_2$F) | 6.55$^{(a)}$ |
| III-6 | Cl | F | —CHCH$_2$—O—CH$_2$CF$_3$ (CH$_3$) | 6.48$^{(a)}$ |

$^{(a)}$ $^1$H-NMR (CDCl$_3$, δ, ppm): in each case a doublet (J = 8 Hz)

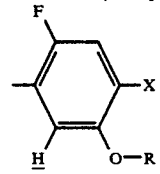

STARTING SUBSTANCES OF THE FORMULA (V)

Example (V-1)

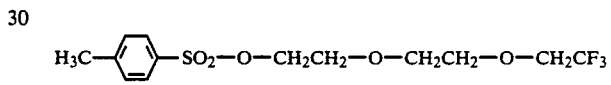

8.0 g (0.1 mol) of pyridine are added at 0° C. to 5° C. to a solution of 9.6 g (0.05 mol) of p-toluenesulphochloride and 9.5 g of 2-(2-(2,2,2-trifluoroethoxy)-ethoxy)-ethanol in 20 ml of dichloromethane. The mixture is subsequently stirred for 3 hours at room temperature and then discharged into 40 g of ice and 15 ml of concentrated hydrochloric acid. The organic phase is separated off, and the aqueous phase is extracted using dichloromethane. The combined organic phases are washed twice with water, dried over magnesium sulphate and freed from solvent in vacuo. 15.4 g (89 % of theory) of 2-(2(2,2,2-trifluoroethoxy)ethoxy-)ethyl p-toluenesulphonate are obtained as a residue as a pale yellow oil. $^1$H-NMR (CDCl$_3$, δ): 7.35 ppm (d, J=8.0 Hz)

The compounds of the formula (V) shown in Table 4 can be prepared analogously below.

(V)

TABLE 4

| Example No. | X$^1$ | R | Physical data |
|---|---|---|---|
| V-2 | H$_3$C—⟨⟩—SO$_2$—O— | —CHCH$_2$—O—CH$_2$CF$_3$ (C$_2$H$_5$) | 7.34$^{(b)}$ |
| V-3 | H$_3$C—⟨⟩—SO$_2$—O— | —CHCH$_2$—O—CH$_2$CF$_3$ (CH$_3$) | 7.34$^{(b)}$ |

TABLE 4-continued

Starting substances of the formula (V)

| Example No. | X¹ | R | Physical data |
|---|---|---|---|
| V-4 | 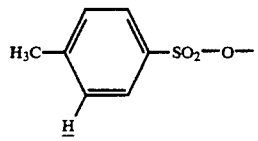 | —CH$_2$CH$_2$—O—CH(CH$_2$F)$_2$ | 7.35(b) |
| V-5 | 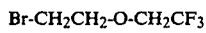 | —CH(CH$_2$F)CH$_2$—O—CH$_2$CF$_3$ | 7.34(b) |

(b) ¹H-NMR (CDCl$_3$, δ, ppm): in each case a doublet (J = 8 Hz) for

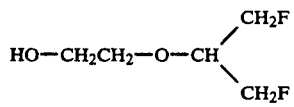

Example (V-6)

Br-CH$_2$CH$_2$-O-CH$_2$CF$_3$ 20 g (0.07 mol) of phosphorus(III) bromide are slowly added dropwise with stirring to a mixture of 28.8 g (0.2 mol) of 2-(2,2,2-trifluoroethoxy)-ethanol, 4 ml of pyridine and 150 ml of diethyl ether. The reaction mixture is first stirred at 0° C. until completion of the addition and then heated to boiling under reflux for 2 hours. It is then mixed cautiously with 100 ml of ice water, and the organic phase is separated off after stirring briefly, washed with 5 % strength sodium hydrogencarbonate solution, dried using sodium sulphate and filtered. The solvent is distilled off from the filtrate and the residue is distilled at normal pressure.

20 g (48.5 % of theory) of 2-(2,2,2-trifluoro-ethoxy)-ethyl bromide of boiling range 112° C. to 116° C. (refractive index: n$_A^{20}$=1.3828) are obtained.

PREPARATION OF 2-(2-fluoro-1-fluoromethyl-ethoxy)ethanol

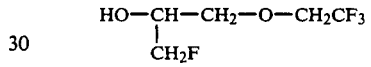

112 g (1.0 mol) of 1,3-difluoro-2-propanol and 3 g of potassium hydroxide are initially introduced and 50 ml of ethylene oxide are condensed in a V4A autoclave (volume : 300 ml) at -78° C. The reaction mixture is then shaken for 12 hours at +80° C. to +90° C. (initial pressure about 9000 hPa). After depressurizing and venting unreacted ethylene oxide, the residual contents of the autoclave are fractionally distilled in a water jet vacuum. 59 g (38 % of theory) of 2-(2-fluoro-1-fluoromethyl-ethoxy)-ethanol are obtained as a main fraction of boiling range 98° C. to 105° C./24 hPa.

¹H-NMR (CDCl$_3$, δ, ppm): 2.75 (Broad s, OH); 3.72 (m, 2×CH$_2$); 3.81 (tq, CH); 4.52 (dm, 2CH$_2$F, J$_{HF}$=47.5 Hz).

PREPARATION OF 1-FLUOROMETHYL-2(2,2,2-TRIFLUOROETHOXY)-ETHANOL

HO—CH(CH$_2$F)—CH$_2$—O—CH$_2$CF$_3$ 0.5 g of sodium are dissolved at 40° C. in 105 g (1.05 mol) of 2,2,2-trifluoroethanol and 76 g (1.0 mol) of epifluorohydrin are subsequently added dropwise at 50° C. to 60° C. in the course of 30 minutes. The reaction mixture is heated to 70° C. with reflux cooling for 18 hours and then fractionally distilled in a water jet vacuum.

114 g (58 % of theory) of 1-fluoromethyl-2-(2,2,2-trifluoroethoxy)-ethanol are obtained as a main fraction of boiling range 70° C. to 75° C./30 hPa.

¹H-NMR (CDCl$_3$, δ, ppm): 3.53 (d, OH, J$_{HH}$=4.7 Hz)); 3.71 (m, OCH$_2$); 3.89 (q, CH$_2$CF$_3$, J$_{HF}$=10.5 HZ); 4.03 (dm, CH); 4.46 (dm, CH$_2$F, J$_{HF}$=46 Ha).

PREPARATION OF 1-ETHYL-2-(2,2,2-TRIFLUOROETHOXY)-ETHANOL

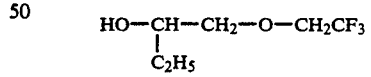

0.5 g of sodium are dissolved at 40° C. in 80 g (0.8 mol) of 2,2,2-trifluoroethanol and 43 g (0.6 mol) of butylene oxide are subsequently added dropwise at 50° C. to 60° C. The reaction temperature is slowly raised to 110° C.; the initially heavy reflux subsides rapidly during the course of this. After 17 hours, the mixture is fractionally distilled in a water jet vacuum. 89 g (86 % of theory) of 1-ethyl-2-(2,2,2-trifluoroethoxy)-ethanol are obtained as a main fraction of boiling range 52° C. to 54° C./24 hPa.

¹H-NMR (CDCl$_3$, δ, ppm): 0.97 (t, CH$_3$); 1.51 (dq, CH$_2$); 2.75 (d, OH, J$_{HH}$=4.8 Hz); 3.41-3.69 (m, CH$_2$O); 3.74 (m, CH); 3.88 (q, CH$_2$CF$_3$, J$_{HF}$=9.9 Hz).

1-Methyl-2-(2,2,2-trifluoroethoxy)-ethanol is obtained analogously

HO—CHCH₂—O—CH₂CF₃
|
CH₃

USE EXAMPLES

In the following use examples, the compound shown below is used as comparison substance:

(A)

(CH₃)₃C, N=N, O, Cl, (CH₃)₂CHO, Cl (structure)

5-tert-butyl-3-(2,4-dichloro-5-isopropoxy.-phenyl)-1,3,4-oxadiazol-2-one (oxadiazone/ ®Ronstar) - known from U.S. Pat. No. 3,835,862.

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the compounds according to Preparation Examples 1, 3, 4, 5, 6 and 7 show a clearly superior action against weeds in comparison with the known compound (A) together with complete tolerability towards wheat.

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example, the compounds according to Preparation Examples 1, 2, 3 and 7 show a clearly superior action against weeds in comparison with the known compound (A) together with good tolerability for wheat.

EXAMPLE C

Defoliation and desiccation of the leaves of cotton

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th true leaf has unfolded completely. In this stage, the plants are sprayed with the preparations of active compound until dripping wet. After 1 week, the shedding of leaves and the desiccation of the leaves are rated, in comparison with the control plants.

In this test, for example, the compounds according to Preparation Examples 1, 2, 3, 4, 5 and 7 show a clear superiority in comparison to the untreated control.

It will be understood that the instant specification and claims are set forth by way of illustration and not limitation, and that various modifications and changes may be made without departing from the spirit and scope of the present invention.

what is claimed is:

1. An N-aryl nitrogen heterocycle having a fluorine-containing substituent of the formula (I)

(structure with Y, Y¹, Y², A, N, X, O—R)

in which
A represents one of the groupings (three cyclohexene/phenyl structures with R¹ and R²)

-continued

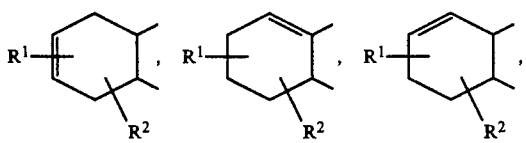

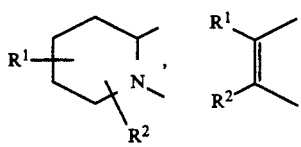

where

R¹ and R² in each case independently of one another represent hydrogen, halogen, halogenoalkyl or alkyl, and Y¹ and Y² in each case represent oxygen or sulphur, R represents in each case optionally branched alkyl, alkenyl, cycloalkyl, cycloalkenyl, cycloalkylalkyl or cyloalkenylalkyl in each case having a carbon-carbon bond interrupted by at least one oxygen atom and in each case substituted by at least one fluorine atom, X represents hydrogen or halogen and Y represents hydrogen or halogen.

2. An N-aryl nitrogen heterocycle having a fluorine-containing substituent according to claim 1, in which A represents one of the groupings

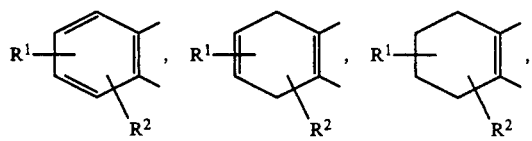

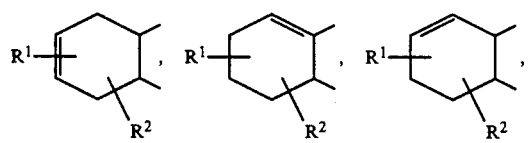

where

R¹ and R² in each case independently of one another represent hydrogen, fluorine, chlorine, bromine or in each case straight-chain or branched alkyl or halogenoalkyl each having 1 to 3 carbon atoms and in the case of halogenoalkyl having 1 to 5 identical or different halogen atoms, and Y¹ and Y² represent oxygen or sulphur, R represents in each case optionally branched alkyl, alkenyl, cycloalkyl, cycloalkenyl, cycloalkylalkyl or cyloalkenylalkyl each having up to 20 carbon atoms and in each case having 1 to 4 carbon-carbon bonds interrupted by 1 to 4 oxygen atoms and in each case substituted by 1 to 5 fluorine atoms, X represents hydrogen, fluorine, chlorine or bromine, and represents hydrogen, fluorine or chlorine.

3. A compound according to claim 1, wherein such compound is 4-chloro-2-fluoro-5-(2-(2,2,2-trifluoroethoxy)-ethoxy)-1-(3,4,5,6-tetrahydrophthalimide)-phenyl of the formula

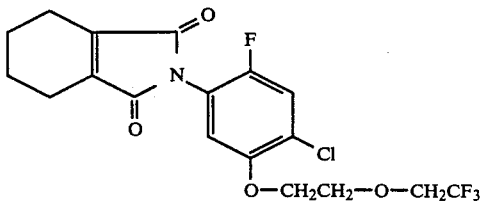

4. A compound according to claim 1, wherein such compound is 4-chloro-2-fluoro-5-(2-(2,2,2-trifluoroethoxy)-ethoxy-1-(2,3-dimethylmaleinimide)-phenyl of the formula

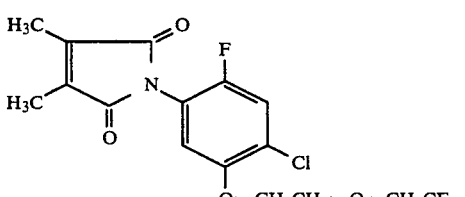

5. A compound according to claim 1, wherein such compound is 4-chloro-2-fluoro-5-(2-[1,3-difluoro-isopropoxyl]-ethoxy-1-(3,4,5,6-tetrahydrophthalimide)-phenyl of the formula

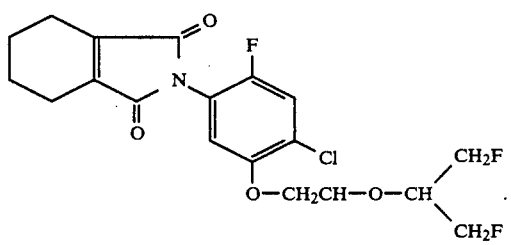

6. A compound according to claim 1, wherein such compound is 4-chloro-2-fluoro-5-(2-[1-methyl-(2,2,2-trifluoroethoxy)]-ethoxy)-1-(3,4,5,6-tetrahydrophthalimid)-phenyl of the formula

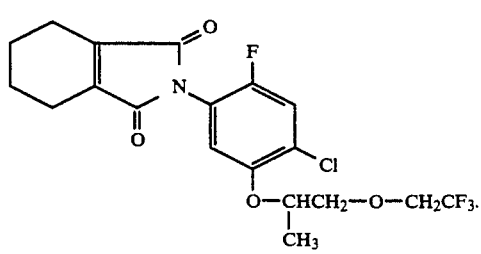

7. A compound according to claim 1, wherein such compound is 4-chloro-2-fluoro-5-(2-[1-ethyl-(2,2,2-trifluoroethoxy)]-ethoxy]-1-(3,4,5,6-tetrahydrophthalimide)-phenyl of the formula

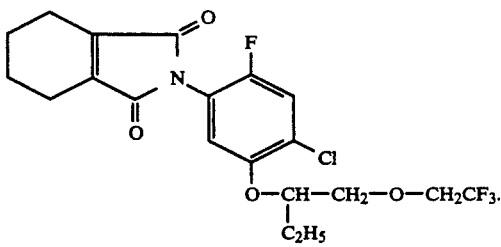

8. A compound according to claim 1, wherein such compound is 4-chloro-2-fluoro-5-(2-(2,2,2-trifluoroethoxy)-ethoxy-ethoxy)-1-(3,4,5,6-tetrahydrophthalimide)-phenyl of the formula

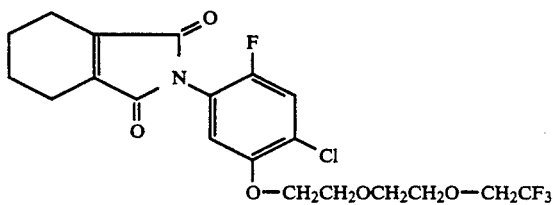

9. A herbicidal composition comprising a herbicidally effective amount of a compound according to claim 1 and a diluent.

10. A method of combating unwanted vegetation which comprises applying to such vegetation or to a locus from which it is desired to exclude such vegetation, a herbicidally effective amount of a compound according to claim 1.

11. The method according to claim 10, wherein such compound is 4-chloro-2-fluoro-S-(2-(2,2,2-trifluoroethoxy)-ethoxy)-1-(S,4,S,6-tetrahydrophthalimide)-phenyl, 4-chloro-2-fluoro-5-(2-(2,2,2-trifluoroethoxy)-ethoxy)-1-(2,3-dimethylmaleinimide)-phenyl, 4-chloro-2-fluoro-5-(2-[1,3-difluoroisopropoxy ]-ethoxy)-1-(3,4,5,6-tetrahydrophthalimide)-phenyl, 4-chloro-2-fluoro-5-(2-[1-methyl-(2,2,2-trifluoroethoxy)-ethoxy])-1-(3,4,5,6-tetrahydrophthalimide)-phenyl, 4-chloro-2fluoro-5-(2[1-ethyl-(2,2,2-trifluoroethoxy)-ethoxy])-1-(3,4,5,6-tetrahydrophthalimide)-phenyl or 4-chloro-2-fluoro-5-(2-(2,2,2-trifluoroethoxy)-ethoxy-ethoxy)-1-(3,4,5,6-tetrahydrophthalimide)-phenyl.

* * * * *

UNITED STATES PATENT AND TRADEMARK OFFICE
CERTIFICATE OF CORRECTION

PATENT NO. : 5,024,694

DATED : June 18, 1991

INVENTOR(S) : Schallner et al.

It is certified that error appears in the above-identified patent and that said Letters Patent is hereby corrected as shown below:

Col. 79, last line    Before " represents " insert -- Y --

Col. 80, line 44    Delete "
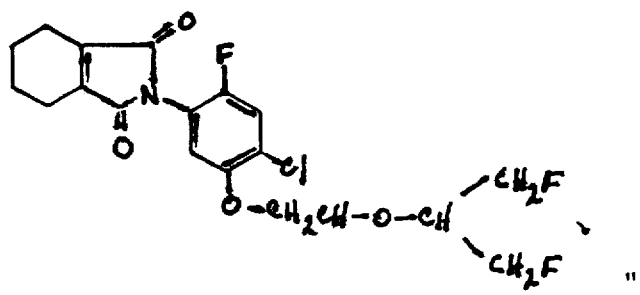
"

and substitute
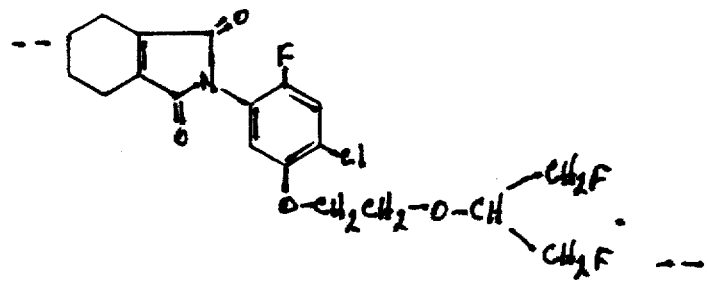

Col. 82, line 11    After " fluoro- " delete " S " and substitute -- 5 --

Col. 82, line 12    Delete " S,4,S,6 " and substitute 3,4,5,6 --

UNITED STATES PATENT AND TRADEMARK OFFICE
CERTIFICATE OF CORRECTION

PATENT NO. : 5,024,694

DATED : June 18, 1991

INVENTOR(S) : Schallner et al.

It is certified that error appears in the above-identified patent and that said Letters Patent is hereby corrected as shown below:

Col. 82, line 20    Delete " 2fluoro-5(2[ " and substitute -- 2-fluoro-5-(2-[ --

Signed and Sealed this

Twentieth Day of April, 1993

Attest:

MICHAEL K. KIRK

Attesting Officer

Acting Commissioner of Patents and Trademarks